(12) United States Patent
Jiao et al.

(10) Patent No.: US 7,749,498 B2
(45) Date of Patent: Jul. 6, 2010

(54) ANTIBODIES FOR INHIBITING BLOOD COAGULATION AND METHODS OF USE THEREOF

(75) Inventors: Jin-an Jiao, Weston, FL (US); Hing C. Wong, Weston, FL (US); Jinghai Wen, Pembroke Pines, FL (US)

(73) Assignee: Genentech, Inc., South San Francisco, CA (US)

( * ) Notice: Subject to any disclaimer, the term of this patent is extended or adjusted under 35 U.S.C. 154(b) by 595 days.

(21) Appl. No.: 10/618,338

(22) Filed: Jul. 11, 2003

(65) Prior Publication Data

US 2005/0089929 A1    Apr. 28, 2005

Related U.S. Application Data

(63) Continuation-in-part of application No. 10/293,417, filed on Nov. 12, 2002, now abandoned, which is a continuation of application No. 09/293,854, filed on Apr. 16, 1999, now Pat. No. 6,555,319, which is a continuation of application No. 08/814,806, filed on Mar. 10, 1997, now Pat. No. 5,986,065.

(51) Int. Cl.
*A61K 39/395* (2006.01)
*C07K 16/00* (2006.01)

(52) U.S. Cl. ............. 424/130.1; 424/133.1; 424/135.1; 424/138.1; 424/141.1; 530/387.1; 530/387.3; 530/388.1; 530/388.22

(58) Field of Classification Search ........................ None
See application file for complete search history.

(56) References Cited

U.S. PATENT DOCUMENTS

| | | | |
|---|---|---|---|
| 4,644,055 A | 2/1987 | Kettner et al. | |
| 4,816,567 A | 3/1989 | Cabilly et al. | |
| 5,122,458 A | 6/1992 | Post et al. | |
| 5,168,062 A | 12/1992 | Stinski | |
| 5,171,662 A | 12/1992 | Sharma | |
| 5,216,132 A | 6/1993 | Basi | 530/387.3 |
| 5,223,427 A * | 6/1993 | Edgington et al. | 435/337 |
| 5,225,539 A | 7/1993 | Winter et al. | |
| 5,385,839 A | 1/1995 | Stinski | |
| 5,437,864 A | 8/1995 | Edgington et al. | 424/145.1 |
| 5,530,101 A | 6/1996 | Queen et al. | |
| 5,534,254 A | 7/1996 | Huston et al. | |
| 5,552,300 A | 9/1996 | Makrides et al. | 435/69.1 |
| 5,589,173 A | 12/1996 | O'Brien et al. | |
| 5,639,641 A | 6/1997 | Pedersen et al. | |
| 5,693,762 A * | 12/1997 | Queen et al. | 530/387.3 |
| 5,766,886 A | 6/1998 | Studnicka et al. | |
| 5,861,267 A | 1/1999 | Su | |
| 5,869,046 A | 2/1999 | Presta et al. | |
| 5,879,677 A | 3/1999 | del Zoppo | |
| 5,889,157 A | 3/1999 | Pastan et al. | |
| 5,958,713 A | 9/1999 | Thastrup et al. | |
| 5,985,279 A | 11/1999 | Waldmann et al. | |
| 5,986,065 A | 11/1999 | Wong et al. | |
| 5,997,867 A | 12/1999 | Waldmann et al. | |
| 6,001,978 A | 12/1999 | Edgington et al. | |
| 6,054,297 A | 4/2000 | Carter et al. | |
| 6,117,639 A | 9/2000 | Germann et al. | |
| 6,245,884 B1 | 6/2001 | Hook | |
| 6,274,142 B1 | 8/2001 | O'Brien et al. | 424/145.1 |
| 6,287,366 B1 | 9/2001 | Derive et al. | |
| 6,309,636 B1 * | 10/2001 | do Couto et al. | 424/133.1 |
| 6,331,415 B1 | 12/2001 | Cabilly et al. | |
| 6,333,167 B1 | 12/2001 | Quinet et al. | |
| 6,555,319 B2 | 4/2003 | Wong et al. | |
| 6,593,291 B1 | 7/2003 | Green et al. | 514/2 |
| 6,610,293 B1 | 8/2003 | Fischer et al. | |
| 6,677,436 B1 | 1/2004 | Sato et al. | |
| 6,703,494 B2 | 3/2004 | Kirchhofer et al. | |
| 6,986,894 B2 | 1/2006 | O'Brien et al. | |
| 2002/0025508 A1 | 2/2002 | Fechteler et al. | |
| 2002/0065327 A1 | 5/2002 | Jiao et al. | |
| 2003/0082636 A1 | 5/2003 | Wong et al. | |
| 2003/0087372 A1 | 5/2003 | DelaCruz et al. | |
| 2003/0109680 A1 | 6/2003 | Wong et al. | |
| 2003/0119075 A1 | 6/2003 | Kirchhofer et al. | |
| 2003/0124117 A1 | 7/2003 | Refino et al. | |
| 2003/0176664 A1 | 9/2003 | Jiao et al. | |
| 2004/0126816 A1 | 7/2004 | Kirchhofer et al. | |
| 2004/0229282 A1 | 11/2004 | Wong et al. | |

(Continued)

FOREIGN PATENT DOCUMENTS

EP    420937 B1    10/1991

(Continued)

OTHER PUBLICATIONS

Cacia et al., Biochemidtry, 1996, vol. 35, pp. 1897-1903.*

(Continued)

*Primary Examiner*—Elizabeth C. Kemmerer
*Assistant Examiner*—Xiaozhen Xie
(74) *Attorney, Agent, or Firm*—Morrison & Foerster LLP

(57) ABSTRACT

Disclosed are antibodies that provide superior anti-coagulant activity by binding native human TF with high affinity and specificity. Also disclosed are methods of using such antibodies to reduce cancer cell tissue factor activity and to detect cancer cells that express TF.

24 Claims, 13 Drawing Sheets

U.S. PATENT DOCUMENTS

| | | | |
|---|---|---|---|
| 2005/0089929 | A1 | 4/2005 | Jiao et al. |
| 2005/0271664 | A1 | 12/2005 | Wong et al. |
| 2006/0039901 | A1 | 2/2006 | Jiao et al. |
| 2006/0159675 | A1 | 7/2006 | Jiao et al. |
| 2006/0235209 | A9 | 10/2006 | Jiao et al. |

FOREIGN PATENT DOCUMENTS

| | | | |
|---|---|---|---|
| EP | 0 239 400 | | 8/1994 |
| EP | 1 069 185 | | 1/2001 |
| JP | 1-503438 | | 11/1989 |
| JP | 4-502408 | T | 5/1992 |
| JP | 2001-516214 | T | 9/2001 |
| WO | WO 89/12463 | | 12/1989 |
| WO | WO-90/07861 | A1 | 7/1990 |
| WO | WO 91/18019 | | 11/1991 |
| WO | WO 94/05328 | | 3/1994 |
| WO | WO 96/13593 | | 5/1996 |
| WO | WO 96/18105 | | 6/1996 |
| WO | WO 96/40921 | | 12/1996 |
| WO | WO 98/40408 | | 9/1998 |
| WO | WO-98/51321 | A1 | 11/1998 |
| WO | WO 99/43713 | | 9/1999 |
| WO | WO-00/18398 | A1 | 4/2000 |
| WO | WO-01/27079 | A2 | 4/2001 |
| WO | WO-01/30333 | A2 | 5/2001 |
| WO | WO 01/70984 | | 9/2001 |
| WO | WO 03/029295 | | 4/2003 |
| WO | WO-03/037911 | | 5/2003 |
| WO | WO-2005/004793 | A2 | 1/2005 |
| WO | WO-2005/004793 | A3 | 1/2005 |
| WO | WO-2005/004793 | C2 | 1/2005 |
| WO | WO-2005/072126 | A2 | 8/2005 |
| WO | WO-2005/072126 | A3 | 8/2005 |

OTHER PUBLICATIONS

Alberts et al., The Cell, 2002, Garland Science, 4th edition, esp. pp. 161, Fig. 3-42.*
Yamashita et al., J. Surg. Oncol., Oct. 25, 2006, [Epub ahead of print].*
Fiore et al., Blood, 1992, vol. 80(12):3127-3134.*
Ngo et al., Int. J. Cancer, 2007, 120:1261-1267.*
C. Schlueter et al., *J. Mol. Biol.*, 256:859-869 (1996).
C. Wulfing et al., *J. Mol. Biol.*, 242:655-669 (1994).
I. Kurucz et al., *Proc. Natl. Acad. Sci. USA*, 90:3830-3834 (1993).
S. Parmley et al., *Gene*, 73:305-318 (1988).
G. Smith et al., *Methods in Enzymology*, 217:228-257 (1993).
W. Soo Hoo et al., *Proc. Natl. Acad. Sci. USA*, 89:4759-4763 (1992).
A. Lin et al., *Science*, 249:677-679 (1990).
N. Gasciogne et al., *Proc. Natl. Acad. Sci. USA*, 84:2936-2940 (1987).
R. Mariuzza et al., *The Journal of Biological*, 264(13):7310-7316 (1989).
J. Kappler et al., *Proc. Natl. Acad. Sci. USA*, 91:8462-8466 (1994).
Rao et al., *Thrombosis Research*, 56:109-118 (1989).
Fiore et al., *Blood*, 80(12):3127-3134 (1992).
Clarke et al., *The Journal of Immunology*, 145:2286-96 (1990).
Ragni et al., *Circulation*, 93:1913-1918 (1996).
George et al., *Marcomolecular Sequencing and Synthesis*, Alan Riss, pp. 127-149 (1988).
Groves et al., *Hybridoma*, 6(1):71-76 (1987).
Illustrated Dictionary of Immunology, Cruse et al., CRC Press (1995).
Morrison, *Ann. Rev. Immunol.*, 10:239-265 (1992).
Carson et al., "An Inhibitory Monoclonal Antibody Against Human Tissue Factor," Blood, 70(2):490-493 (1987).
Caulfield, M.J. et al. "A pathogenic monoclonal antibody, G8, is characteristic of antierythrocyte autoantibodies from Coombs'-positive NZB mice," J. Immunol. 148(7):2068-2073 (1992).
Database EMBL: MMG8LC, Accession #X60425, Oct. 21, 1991 Description "G8 (Anti-MRBC) V(L), J(L)" XP-002305737.

Presta et al., "Generation of a Humanized, High Affinity Anti-Tissue Factor Antibody for Use as a Novel Antithrombotic Therapeutic," Thromb Haemost 85:379-89 (2001).
Wen Jinghai et al. "Antibody-dependent cellular cytotoxicity and antibody dependent cellular phgocytosis of breast cancer cells mediated by anti-tissue factor monoclonal antibodies," FASEB Journal, 15(5):A1198 (2001) Annual Meeting of the Federation of American Societies for Experimental Biology on Experimental Biol; Orlando, Florida, Mar. 31-Apr. 4, 2001 Abstract.
Albrecht et al., "An ELISA for tissue factor using monoclonal antibodies," Blood Coagulation and Fibrinolysis, 3:263-270 (1992).
Almus et al., "Properties of Factor VIIa/Tissue Factor Complexes in an Umbilical Vein Model," Blood, 76(2):354-360 (1990).
Ardaillou et al., "Glomerular tissue factor stimulates thromboxane synthesis in human platelets via thrombin generation," Kidney International, 41:361-368 (1992).
Barstad et al., "Procoagulant Human Monocytes Mediate Tissue Factor/Factor VIIa-Dependent Platelet-Thrombus Formation When Exposed to Flowing Nonanticoagulated Human Blood," Arteriosclerosis, Thrombosis, and Vascular Biology, 15(1):11-16 (1995).
Beers et al., The Merck Manual of Diagnosis and Therapy, $17^{th}$ edition, 1999, Merck Research Laboratories, pp. 1654-1681.
Benedict et al., "Monoclonal Antibody to Tissue Factor Inhibits Intravascular Thrombosis without Imparing Extravascular Hemostasis," JACC, Feb. 1995 Abstract 1012-104, p. 366A.
Bjoern et al., "Human Plasma and Recombinant Factor VII," The Journal of Biological Chemistry, 266(17):11051-11057 (1991).
Broze, George J., Jr., "Binding of Human Factor VII and VIIa to Monocytes," J. Clin. Invest., 70:526-535 (1982).
Carson et al., "Monoclonal Antibodies Against Bovine Tissue Factor, Which Block Interaction With Factor VII," Blood, 66(1):152-156 (1985).
Cate et al., "The Activation of Factor X and Prothrombin by Recombinant Factor VIIa in Vivo Is Mediated by Tissue Factor," The Journal of Clinical Investigation, Inc., 92:1207-1212 (1993).
Chapman et al., "Regulation of the Procoagulant Activity within the Bronchoalveolar Compartment of Normal Human Lung," Am. Rev. Respir. Dis., 137(6):1417-1425 (1988).
Chattopadhyay et al., "Molecular Recognition Sites on Factor Xa Which Participate in the Prothrombinase Complex," The Journal of Biological Chemistry, 267(17):12323-12329 (1992).
Clarke et al., "The first epidermal growth factor domain of human coagulation factor VII is essential for binding with tissue factor," FEBS, 298(2,3):206-310 (1992).
Collen et al., "New thrombolytic agents and strategies," Bailliere's Clinical Haematology, 8(2):425-435 (1995).
Colman, P.M., "Effects of amino acid sequence changes on antibody-antigen interactions," Research in Immunology, 145:33-36 (1994).
Contrino et al., "In Situ Characterization of Antigenic and Functional Tissue Factor Expression in Human Tumors Utilizing Monoclonal Antibodies and Recombinant Factor VIIa as Probes," Americal Journal of Pathology, 145(6):1315-1322 (1994).
Drake et al., "Functional Tissue Factor Is Entirely Cell Surface Expressed on Lipopolysaccharide-stimulated Human Blood Monocytes and a Constitutively Tissue Factor-producing Neoplastic Cell Line," The Journal of Cell Biology, 109:389-395 (1989).
Drake et al., "Selective Cellular Expression of Tissue Factor in Human Tissues," American Journal of Pathology, 134(5):1087-1097 (1989).
Fair et al., Cooperative Interaction Between Factor VII and Cell Surface-Expressed Tissue Factor, The Journal of Biological Chemistry, vol. 262, Aug. 25, 1987, pp. 11692-11698.
Faulk et al., "Tissue Factor: Identification and Characterization of Cell Types in Human Placentae," Blood, 76(1):86-96 (1990).
Fay et al., "Mutating factor VIII: lessons from structure to function," Blood Reviews, 19:15-17 (2005).
Flössel et al., "Immunohistochemical detection of tissue factor (TF) on paraffin sections of routinely fixed human tissue," Histochemistry, 101:449-453 (1994).

Gouault-Heilmann et al., "The Procoagulant Factor of Leukaemic Promyelocytes: Demonstration of Immunologic Cross Reactivity with Human Brain Tissue Factor," British Journal of Haematology, 30:151-158 (1975).

Grabowski et al., "The Functional Expression of Tissue Factor by Fibroblasts and Endothelial Cells Under Flow Conditions," Blood, 81(2):3265-3270 (1993).

Hamaguchi et al., "FDP D-Dimer Induces the Secretion of Interleukin-1, Urokinase-Type Plasminogen Activator, and Plasminogen Activator Inhibitor-2 in a Human Promonocytic Leukemia Cell Line," Blood, 77(1):94-100 (1991).

Hoffman et al., "Human Monocytes Support Factor X Activation by Factor VIIa, Independent of Tissue Factor: Implications for the Therapeutic Mechanism of High-Dose Factor VIIa in Hemophilia," Blood, 83(1):38-42 (1994).

Huang et al., "The Mechanism of an Inhibitory Antibody on TF-initiated Blood Coagulation Revealed by the Crystal Structures of Human Tissue Factor, Fab 5G9 and TF 5G9 Complex," J. Mol. Biol., 275:873-894 (1998).

Imamura et al., "Role of Macrophage Tissue Factor in the Development of the Delayed Hypersensitivity Reaction in Monkey Skin," Cellular Immunology, 152:614-622 (1993).

Ito et al., "Characterization of Functionally Important Regions of Tissue Factor by Using Monoclonal Antibodies," J. Biochem., 114(5):691-696 (1993).

James et al., "Inhibition of tissue factor activity reduces the density of cellular network formation in an in vitro model of angiogensis," Biochemical Society Transactions, 30(2):217-221 (2002).

Jang et al., "Antithrombotic Effect of a Monoclonal Antibody Against Tissue Factor in a Rabbit Model of Platelet-Mediated Arterial Thrombosis," Arteriosclerosis and Thrombosis, 12(8):948-954 (1992).

Kirchhofer et al., "The Tissue Factor Region That Interacts with Factor Xa in the Activation of Factor VII," Biochemistry, 40:675-682 (2001).

Kumar et al., "Identification of Molecular Sites on Factor VII Which Mediate Its Assembly and Function in the Extrinsic Pathway Activation Complex," The Journal of Biological Chemistry, 266(2):915-921 (1991).

Kumar et al., "Specific molecular interaction sites on factor VII involved in factor X activation," Eur. J. Biochem. 217:509-518 (1993).

Levi et al., "Inhibition of Endotoxin-induced Activation of Coagulation and Fibrinolysis by Pentoxifylline or by a Monoclonal Anti-tissue factor Antibody in Chimpanzees," The Journal of Clinical Investigation, Inc., 93:114-120 (1994).

Maekawa et al., "Complement-Dependent Immunosuppressive Anti-Tissue Factor Monoclonal Antibody: The Establishment of Monoclonal Antibodies and Their Effect on Mixed Lymphocyte Reaction," Transplantation Proceedings, 25(4):2713-2715 (1993).

Martin et al., "Activation of Factor X by Factor VIIa on Monocyte Cell Surfaces," pp. 3828-3829 Blood. Jun. 15, 1994;83(12):3828-9.

Martin et al., "Tissue Factor: molecular recognition and cofactor function," The FASEB Journal, 9:852-859 (1995).

Masuda et al., "Association of tissue factor with a γ chain homodimer of the IgE receptor type I in cultured human monocytes," Eur. J. Immunol., 26:2529-2532 (1996).

McGee et al., "Functional Difference between Intrinsic and Extrinsic Coagulation Pathways," The Journal of Biological Chemistry, 266(13):8079-8085 (1991).

Merriam-Webster Online dictionary, downloaded Oct. 11, 2005, world wide web at m-w.com, definition of thrombosis, 2 pages.

Morrissey et al., "Monoclonal Antibody Analysis of Purified and Cell-Associated Tissue Factor," Thrombosis Research, 52:247-261 (1988).

Morrissey et al., "Resolution of Monomeric and Heterodimeric Forms of Tissue Factor, the High-Affinity Cellular Receptor for Factor VII," Thrombosis Research, 50:481-493 (1988).

Mueller, Barbara M., Expression of Tissue Factor by Melanoma Cells Promotes Efficient Hematogenous Metastasis, Proc. Natl. Acad. Sci. USA, Dec. 1992, vol. 89, pp. 11832-11836.

Muller et al., "Structure of the Extracellular Domain of Human Tissue Factor: Location of the Factor VIIa Binding Site,".

Nemerson et al., "An Ordered Addition, Essential Activation Model of the Tissue Factor Pathway of Coagulation: Evidence for a Conformational Cage," Biochemistry, 25:4020-4033 (1986).

Noguchi et al., "Correlation Between Antigenic and Functional Expression of Tissue Factor on the Surface of Cultured Human Endothelial Cells Following Stimulation by Lipopolysaccharide Endotoxin," Thrombosis Research, 55:87-97 (1989).

Østerud et al., "The Interaction of Human Blood Coagulation Factor VII and Tissue Factor: The Effect of Anti Factor VII, Anti Tissue Factor and Diisopropylfluorophosphate," Biochemical and Biophysical Research Communications, 88(1):59-67 (1979).

Pawashe et al., "A Monoclonal Antibody Against Rabbit Tissue Factor Inhibits Thrombus Formation in Stenotic Injured Rabbit Carotid Arteries," Circulation Research, Jan. 1994, vol. 74, No. 1, pp. 56-63.

Ploplis et al., "Initiation of the Extrinsic Pathway of Coagulation—Association of Factor VIIa with a Cell Line Expressing Tissue Factor," The Journal of Biological Chemistry, Jul. 15, 1987, vol. 262, pp. 9503-9508.

Price et al., "Tissue factor and tissue factor pathway inhibitor," Anaesthesia, 59:483-492 (2004.

Rehemtulla et al., "The Integrity of the Cysteine 186-Cysteine 209 Bond of the Second Disulfide Loop of Tissue Factor Is Required for Binding of Factor VII," The Journal of Biological Chemistry, Jun. 5, 1991, vol. 266, No. 16, pp. 10294-10299.

Ruf et al., "An Anti-Tissue Factor Monoclonal Antibody Which Inhibits TF-VIIa Complex Is a Potent Anticoagulant in Plasma," Thrombosis and Haemostasis, 66(5):529-533 (1991).

Ruf et al., "Antibody Mapping of Tissue Factor Implicates Two Different Exon-Encoded Regions in Function," Biochem J. (1991) 278, pp. 729-733.

Ruf et al., "Characterization of Factor VII Association with Tissue Factor in Solution—High and Low Affinity Calcium Binding Sites in Factor VII Contribute to Functionally Distinct Interactions," The Journal of Biological Chemistry, vol. 266, Aug. 25, 1991, pp. 15719-15725.

Ruf et al., "Phospholipid-independent and -dependent Interactions Required for Tissue Factor Receptor and Cofactor Function," The Journal of Biological Chemistry, Feb. 5, 1991, vol. 266, pp. 2158-2166.

Ruf et al., "Structural Biology of Tissue Factor, the Initiator of Thrombogenesis in Vivo," The FASEB Journal, Apr. 1994, vol. 8, pp. 385-390.

Ruf et al., "Tissue Factor Residues 157-167 Are Required for Efficient Proteolytic Activation of Factor X and Factor VII," The Journal of Biological Chemistry, Nov. 5, 1992, vol. 267, No. 31, pp. 22206-22210.

Ruf et al., "Two Sites in the Tissue Factor Extracellular Domain Mediate the Recognition of the Ligand Factor VIIa," Proc. Natl. Acad. Sci. USA, Oct. 1991, vol. 88, pp. 8430-8434.

Ryan et al., "Tumor Necrosis Factor-Induced Endothelial Tissue Factor Is Associated With Subendothelial Matrix Vesicles But Is Not Expressed on the Apical Surface," Blood, Aug. 15, 1992, vol. 80, No. 4, pp. 966-974.

Sakai et al., "Binding of Human Factors VII and VIIa to a Human Bladder Carcinoma Cell Line (J82)—Implications For The Initiation of the Extrinsic Pathway of Blooad Coagulation," The Journal of Biological Chemistry, vol. 264, No. 17, Jun. 15, 1989, pp. 9980-9988.

Salatti et al., "Modulation of Procoagulant Activity of Extracellular Endothelial Matrix by Anti-Tissue Factor Antibody and the Synthetic Peptide Arg-Gly-Asp-Val. Experiments with Flowing Non-Anticoagulated Human Blood," Blood Coagulation and Fibrinolysis, 1993, vol. 4, pp. 881-890.

Sandset et al., "Immunodepletion of Extrinsic Pathway Inhibitor Sensitizes Rabbits to Endotoxin-lnduced Intravascular Coagulation and the Generalized Shwartzman Reaction," Blood, Sep. 15, 1991, vol. 78, No. 6, pp. 1496-1502.

Speidel et al., "Procoagulant Activity on Injured Arteries and Associated Thrombi Is Mediated Primarily by the Complex of Tissue Factor and Factor VIIa, Pathophysiology and Natural History," Coronary Artery Disease, Jan. 1996, vol. 7, No. 1, pp. 57-60.

Stephens et al., "Production of Tissue Factor By Monocyte Porgenitor Cells," Thrombosis Research, 1994, vol. 76, No. 1, pp. 33-45.

Sturm et al., "Immunohistological Detection of Tissue Factor in Normal and Abnormal Human Mammary Glands Using Monoclonal Antibodies," Virchows Archiv A Pathological Anatomy and Histopathology, 1992, 421:79-86.

Toomey et al., "Localization of the Human Tissue Factor Recognition Determinant of Human Factor VIIa," The Journal of Biological Chemistry, Oct. 15, 1991, vol. 266, No. 29, pp. 19198-19202.

Tsao et al., "Monocytes Can Be Induced by Lipopolysaccharide-Triggered T Lymphocytes To Express Functional Factor VII/VIIa Protease Activity," J. Exp. Med., Apr. 1984, vol. 159, pp. 1042-1057.

Tsuda et al., "Development of Antitissue Factor Antibodies in Patients After Liver Surgery," Blood, vol. 82, No. 1 Jul. 1, 1993, pp. 96-102.

Walsh et al., "Discordant Expression of Tissue Factor Antigen and Procoagulant Activity on Human Monocytes Activated with LPS and Low Dose Cycloheximide," Thrombosis and Haemostasis, 1991, 66 (5), pp. 552-558.

Warr et al., "Disseminated Intravascular Coagulation in Rabbits Induced by Administration of Endotoxin or Tissue Factor: Effect of Anti-Tissue Factor Antibodies and Measurement of Plasma Extrinsic Pathway Inhibitor Activity," Blood, vol. 75, No. 7, Apr. 1, 1990, pp. 1481-1489.

Camerer et al., "Tissue Factor—And Factor X-Dependent Activation of Protease-Activated Receptor 2 by Factor VIIa," PNAS, 97(10):5255-5260 (2000).

Ruf et al., "Tissue Factor Signaling," Thrombosis and Haemostasis, 82(2):175-182 (1999).

Ollivier et al., "Tissue Factor-Dependent Vascular Endothelial Growth Factor Production by Human Fibroblasts in Response to Activated Factor VII," Blood, 91(8):2698-2703 (1998).

Wiiger et al., "Effects of Binding of Ligand (FVIIa) to Induced Tissue Factor in Human Endothelial Cells," Thrombosis Research, 98:311-321 (2000).

Konigsberg et al., "The TF:VIIa Complex: Clinical Significance, Structure-Function Relationships and Its Role in Signaling and Metastasis," Thrombosis Haemostasis, 86:757-771 (2001).

Riewald et al., "Mechanistic Coupling of Protease Signaling and Initiation of Coagulation by Tissue Factor," PNAS, 98(14):7742-7747 (2001).

Mueller et al, "Expression of Tissue Factor by Melanoma Cells Promote Efficient Hematogenous Metastasis," Proc. Natl. Acad. Sci. USA, 89:11832-11836 (1992).

Poster Presentation Experimental Biology 2001, Mar. 31-Apr. 4, 2001, Orlando, Florida, Anti-Tissue Factor Antibodies.

Francis et al., "Effect of Antihemostatis Agents on Experimental Tumor Dissemination," Sem. in Thrombosis and Haemostasis, 28(1):29-38 (2002).

Amirkhosravi et al., Suppl. to J. of Thrombosis and Haemostasis Abstract:OC1021 (2001).

Benhar et al., "Rapid Humanization of the Fv of Monoclonal Antibody B3 by Using Framework Exchange of the Recombinant Immunotoxin B3(Fv)-PE38," Proc. Natl. Acad. Sci. USA, 91:12051-12055 (1994).

Booy et al., "Monoclonal and bispecific antibodies as novel therapeutics," Arch. Immunol. Ther. Exp., 54:85-101 (2006).

Boulianne et al., "Production of functional chimaeric mouse/human antibody," Nature, 312:643-646 (1984).

Bruggemann et al., "The Immunogenicity of Chimeric Antibodies," J. Exp. Med. 170:2153-2157 (1989).

Carter et al., "Humanization of an anti-p185HER2 antibody for human cancer therapy," Proc. Natl. Acad. Sci. USA, 89:4285-4289 (1992).

Casipit et al., "Improving the binding affinity of an antibody using molecular modeling and sit directed mutagenesis," Protein Science, 7:1671-1680 (1998).

Chothia et al., "The outline structure of the T-Cell $\alpha\beta$ receptor," The EMBO Journal, 7(12):3745-3755 (1988).

Co et al., "Humanized antibodies for antiviral therapy," Proc. Natl. Acad. Sci. USA, 88:2869-2873 (1991).

Couto et al., "Anti-BA46 Monoclonal Antibody Mc3: Humanization Using a Novel Positional Consensus and In Vivo and In Vitro Characterization," Cancer Research, 55:1717-1722 (1995).

Couto et al., "Designing Human Consensus Antibodies with Minimal Positional Templates," Cancer Research (Suppl.) 55:5973s-5977s (1995).

Faber et al., "A Novel Method to Determine the Topology of Peroxisomal Membrane Proteins in Vivo Using the Tobacco Etch Virus Protease," The Journal of Biological Chemistry, 276(39):36501-36507 (2001).

Foote et al., "Antibody Framework Residues Affecting the Conformation of the Hypervariable Loops," J. Mol. Biol., 224:487-499 (1992).

Gorman et al., "Reshaping a therapeutic CD4 Antibody," Proc. Natl. Acad. Sci. USA, 88:4181-4185 (1991).

Gregoire et al., "Engineered secreted T-cell receptor $\alpha\beta$ heterodimers," Proc. Natl. Acad. Sci. USA, 88:8077-8081 (1991).

Griffiths et al., "Human anti-self antibodies with high specificity from phage display libraries," The EMBO Journal, 12(2):725-734 (1993).

Hanes et al., "Picomolar affinity antibodies from a fully synthetic naïve library selected and evolved by ribosome display," Nature Biotechnology, 18:1287-1292 (2000).

Jager et al., Current Status of Cancer Immunodetection with Radiolabeled Human Monoclonal Antibodies, Seminars in Nuclear Medicine, vol. XXIII, No. 2, 165-179 (1993).

Janeway et al., Immunobiology, third edition, Garland Press, pp. 3:7-3:11 (1997).

Kao et al., "Chimeric Antibodies with Anti-Dextran-Derived Complementarity-Determining Regions and Anti-p-Azophenylarsonate-Derived Framework Regions," The Journal of Immunology, 151:1968-1979 (1993).

Knappik et al., "Fully Synthetic Human Combinatorial Antibody Libraries (HuCAL) based on Modular Consensus Frameworks and CDRs Randomized with Trinucleotides," J. Mol. Biol., 296:57-86 (2000).

Leong et al., "Adapting pharmacokinetic properties of a humanized anti-interleukin-8 antibody for therapeutic applications using site-specific pegylation," Cytokine, 16(3):106-119 (2001).

LoBuglio et al., "Mouse/human chimeric monoclonal antibody in man: Kinetics and immune response," Proc. Natl. Acad. Sci. USA, 86:4220-4224 (1989).

Mateo et al., "Humanization of a mouse monoclonal antibody that blocks the epidermal growth factor receptor: recovery of antagonistic activity," Immunotechnology, 3:71-81 (1997).

Morrison et al., "Chimeric human antibody molecules: Mouse antigen-binding domains with human constant region domains," Proc. Natl. Acad. Sci. USA, 81:6851-6855 (1984).

Morrison et al., "Genetically Engineered Antibody Molecules," Advances in Immunology, 44:65-93.

Novotny et al., "A soluble, single-chain T-cell receptor fragment endowed with antigen-combining properties," Proc. Natl. Acad. Sci. USA, 88:8646-8650 (1991).

Onda et al., "A phage display system for detection of T cell receptor-antigen interactions," Molecular Immunology, 32(17-18):1387-1397 (1995).

Owens et al., "The Generic Engineering of Monoclonal Antibodies," Journal of Immunological Methods, 168:149-165 (1994).

Padlan, "A possible procedure for reducing the immunogenicity of antibody variable domains while preserving their ligand-binding properties," Mol. Immun., 28(4/5):489-498 (1991).

Padlan, "Anatomy of the antibody molecule," Molecular Immunology, 31(3):169-217 (1994).

Padlan, "On the Nature of Antibody Combining Sites: Unusual Structural Features That May Confer on These Sites an Enhanced Capacity for Binding Ligands," Proteins, 7:112-124 (1990).

Queen et al., "A humanized antibody that binds to the interleukin 2 receptor," Proc. Natl. Acad. Sci. USA, 86:10029-10033 (1989).

Queen et al., "Cell-Type Specific Regulation of a k Immunoglobin Gene by Promoter and Enhancer Elements," Immunological Reviews, 89:49-68 (1986).

Rangel-Frausto, M. Sigfrido, "Sepsis: Still Going Strong," Archives of Medical Research, 36:672-681 (2005).

Reichart, "Monoclonal antibodies in the clinic," Nature Biotechnology, 19:819-822 (2001).

Reichmann et al., "Reshaping human antibodies for therapy," Nature, 332:323-327 (1988).
Robertson, "Genentech awarded critical antibody patent," Nature Biotechnology, 20:108 (2002).
Roguska et al., "A comparison of two murine monoclonal antibodies humanized by CDR-grafting and variable domain resurfacing," Protein Engineering, 9(10):895-904 (1996).
Roguska et al., "Humanization of murine monoclonal antibodies through variable domain resurfacing," Proc. Natl. Acad. Sci. USA, 91:969-973 (1994).
Rudikoff et al., "Single amino acid substitution altering antigen-binding specificity," Proc. Natal. Acad. Sci. USA, 79:1979-1983 (1982).
Saldanha et al., "A single backmutation in the human kIV framework of a previously unsuccessfully humanized antibody restores the binding activity and increases the secretion in cos cells," Molecular Immunology, 36:709-719 (1999).
Shearman et al., "Construction, expression and characterization of humanized antibodies directed against the human α/β T cell receptor," The Journal of Immunology, 147:4366-4373 (1991).
Tan et al., "Superhumanized Antibodies: Reduction of Immunogenic Potential by Complementarity-Determining Region Grafting with Human Germline Sequences: Application to an Anti-CD28," The Journal of Immunology, 169:1119-1125 (2002).
Taylor et al., "Protein C Prevents the Coagulopathic and Lethal Effects of *Escherichia coli* Infusion in the Baboon," J. Clin. Invest., 79:918-925 (1987).
Taylor, F.B., "Staging of the pathophysiologic responses of the primate microvasculature to *Escherichia coli* and endotoxin: examination of the elements of the compensated response and their links to the corresponding uncompensated lethal variants," Crit. Care Med., 29( &):S78-89 (2001).
Tempest et al., "Reshaping a human monoclonal antibody to inhibit human respiratory syncytial virus infection in vivo," Bio/Technology, 9:266-271 (1991).
Teng et al., "Construction and testing of mouse-human hetermyelomas for human monoclonal antibody production," Proc. Natl., Acad. Sci. USA, 80:7308-7312 (1983).
Tomizuka et al., "Double trans-chromosomic mice: Maintenance of two individual human chromosome fragments containing Ig heavy and k lock and expression of fully human antibodies," PNAS, 97(2):722-727 (2000).
Vaughan et al., "Human Antibodies with Sub-nanomolar Affinities Isolated from a Large Non-immunized Phage Display Library," Nature Biotechnology, 14:309-314 (1996).
Verhoeyen et al., "Reshaping Human Antibodies: Grafting an Antilysozyme Activity," Science, 239:1534-1536 (1988).
Ward, E. S., "Expression and Secretion of T-Cell Receptor Vα and Vβ Domains using *Escherichia coli* as a Host," Scand. J. Immunol., 34:215-220 (1991).
Watson et al., Molecular Biology of the Gene, fourth edition, The Benjamin/Cummings Publishing Company, Inc., p. 840 (1987).
Bernard, Gordon R. et al., "Efficacy and Safety of Recombinant Human Activated Protein C for Severe Sepsis," The New England Journal of Medicine 344:699-709 (2001).
Bird et al., "Single-Chain Antigen-Binding Proteins," Science 242(4877):423-6 (1988).
Bokarewa et al., "Intra-articular tissue factor/factor VII complex induces chronic arthritis," Inflamm Res. 51(9):471-7 (2002).
Busso et al., "Role of the Tissue Factor Pathway in Synovial Inflammation," Arthritis Rheum 48(3):651-9 (2003).
Furmaniak-Kazmierczak et al., "Studies of Thrombin-induced Proteoglycan Release in the Degradation of Human and Bovine Cartilage," J. Clin. Invest. 94:472-480 (1994).
Huston et al., "Protein engineering of antibody binding sites: Recovery of specific activity in an anti-digoxin single-chain Fv analogue produced in *Escherichia coli*," Proc. Natl. Acad. Sci. USA 85:5879-5883 (1988).
Jones et al., "Replacing the complementarity-determining regions in a human antibody with those from a mouse," Nature 321:522-525 (1986).

Junghans et al., Pharmacokinetics and bioactivity of 1, 4, 7, 10-tetraazacylododecane off, N'', N'''-tetraacetic acid (DOTA)-bismuth-conjugated anti-Tac antibody for alpha-emitter (212Bi) therapy, Cancer Research 53(23):5683-9 (1993).
Kincaid-Smith, Priscilla, "Participation of intravascular coagulation in the pathogenesis of glomerular and vascular lesions," Kidney International 7:242-253 (1975).
Kozbor et al., "The production of monoclonal antibodies from human lymphocytes," Immunology Today, 4:72-79 (1983).
Marty et al., "Amelioration of collagen-induced arthritis by thrombin inhibition," Journal of Clin. Invest. 107(5):631-640 (2001).
Matthay, Michael A., "Severe Sepsis—A New Treatment with Both Anticoagulant and Antiinflammatory Properties," The New England Journal of Medicine 344:759-762 (2001).
Mechtcheriakova et al., "Specificity, diversity, and convergence in VEGF and TNF-α signaling events leading to tissue factor up-regulation via EGR-1 in endothelial cells," The FASEB Journal 15:230-242 (2001).
Minnema et al., "Recombinant human antrithrombin III improves survival and attenuates inflammatory responses in baboons lethally challenged with *Escherichia coli*," Blood 95(4):1117-1123 (2000).
More et al., "Immunohistochemical study of tissue factor expression in normal intestine and idiopathic inflammatory bowel disease," J. Clin. Pathol. 46:703-708 (1993).
Morris et al., "Thrombin in inflammation and healing: relevance to rheumatoid arthritis," Annals of the Rheumatic Diseases 53:72-79 (1994).
Morrison, Sherie, "Transfectomas Provide Novel Chimeric Antibodies," Science 229:1202-1207 (1985).
Nakano et al., "Characteristics of the protease activity in synovial fluid from patients with rheumatoid arthritis and osteoarthritis," Clinical and Experimental Rheumatology 17:161-170 (1999).
Oi, V.T. et al., "Chimeric Antibodies," BioTechniques, 4(3):214-221 (1986).
Olsson and Kaplan, "Human-Human Monoclonal Antibody-Producing Hybridomas: Technical Aspects," Methods in Enzymology 92:3-16 (1983).
Osterud et al., "Induction of Tissue Factor Expression in Whole Blood: Lack of Evidence for the Presence of Tissue Factor Expression in Granulocytes," Thromb Haemost 83:861-7 (2000).
Schopf et al., "Enhanced procoagulant activity of mononuclear leukocytes in patients with atopic dermatitis and psoriasis," Arch Dermatol Res, 285:305-309 (1993).
Segal et al. "Tissue Factor Activity in Patients with Systemic Lupus Erythematosus: Association with Disease Activity," The Journal of Rheumatology 27:2827-2832 (2000).
Shen et al., "Vascular Endothelial Growth Factor KDR Receptor Signaling Potentiates Tumor Necrosis Factor-induced Tissue Factor Expression in Endothelial Cells," The Journal of Biological Chemistry 276(7):5281-5286 (2001).
Varisco et al., "Effect of thrombin inhibition on synovial inflammation in antigen induced arthritis," Annal of Rheumatic Diseases 59:781-787 (2000).
Wakefield et al., "Immunohistochemical study of vascular injury in acute multiple sclerosis," J. Clin. Pathol. 47:129-133 (1994).
Webber et al., "Preparation and Characterization of a Disulfide-Stablized Fv Fragment of the Anti-Tac Antibody: Comparison with its Single-Chain Analog," Molecular Immunology 32(4):249-258 (1995).
Weinberg et al., "Extravascular Fibrin Formation and Dissolution in Synovial Tissue of Patients with Osteoarthritis and Rheumatoid Arthritis," Arthritis and Rheumatism 34(8):996-1005 (1991).
Welty-Wolf et al., "Coagulation Blockade Prevents Sepsis-induced Respiratory and Renal Failure in Baboons," American Journal of Respiratory and Critical Care Medicine 164:1988-1996 (2001).
Zeher et al., "Fibrinolysis-Resistant Fibrin Deposits in Minor Labial Salivary Glands of Patients with Sjogren's Syndrome," Clinical Immunology and Immunopathology 71(2):149-155 (1994).
Asadullah et al., "The Pathophysiological Role of Cytokines in Psoriasis," Drugs of Today, 35(12):913-924 (1999).
Carraway et al., "Blockade of Tissue Factor," American Journal of Respiratory and Critical Care Medicine, 167:1200-1209 (2003).

Erlich et al., "Tissue Factor Initiates Glomerular Fibrin Deposition and Promotes Major Histocompatibility Complex Class II Expression in Crescentic Glomerulonephritis," American Journal of Pathology, 150(3):873-880 (1997).

Esmon, Charles T., "Role of Coagulation Inhibitors in Inflammation," Thrombosis and Haemostasis, 86(1):51-56 (2001).

Houston, Donald S., "Tissue factor—a therapeutic target for thrombotic disorders," Expert Opinion on Therapeutic Targets, Ashley Publications, 6(2):159-174 (2002).

Ishihara et al., "IL-6 in automimmune disease and chronic inflammatory proliferative disease," Cytokine & Growth Factor Reviews, 13(4-5):357-368 (2002).

Maimone et al., "T Cell Lymphokine-induced Secretion of Cytokines by Monocytes from Patients with Multiple Sclerosis," Cellular Immunology, 146:96-106 (1993).

Miller et al., "Extrinsic Coagulation Blockade Attenuates Lung Injury and Proinflammatory Cytokine Release after Intratracheal Lipopolysaccharide," American Journal of Respiratory Cell and Molecular Biology, American Lung Association, 26(6):650-658 (2002).

Skopouli et al., "Cytokines in Sjogren's syndrome," Annales de Medecine Interne, Masson, Paris, 146(4):219-222 (1995).

Welty-Wolf et al., "Tissue Factor in Experimental Acute Lung Injury," Seminars in Hematology, 38(4):35-38 (2001).

Final Office Action mailed Dec. 10, 2007, for U.S. Appl. No. 11/087,528, filed Mar. 22, 2005, by Wong et al., 12 pages.

Faelber, K. et al. (Oct. 12, 2001). "The 1.85 Å Resolution Crystal Structures of Tissue Factor in Complex with Humanized Fab D3h44 and of Free Humanized Fab D3h44: Revisiting the Solvation of Antigen Combining Sites," *J. Mol. Biol.* 313(1):83-97.

Kirchhofer, D. et al. (Dec. 2000). "Epitope Location on Tissue Factor Determines the Anticoagulant Potency of Monoclonal Anti-Tissue Factor Antibodies," *Thrombosis and Haemostatis* 84(6):1072-1081.

Berzofsky, J.A. et al. (1993). "Immunogenicity and Antigen Structure," Chapter 8 in *Fundamental Immunology*, Paul, W.E. editor, Raven Press: New York, NY, p. 242.

Final Office Action mailed Sep. 9, 2004, for U.S. Appl. No. 09/990,586, filed Nov. 21, 2001, 2 pages.

Final Office Action mailed Sep. 6, 2006, for U.S. Appl. No. 10/310,113, filed Dec. 4, 2002, 18 pages.

Final Office Action mailed Sep. 6, 2006, for U.S. Appl. No. 11/087,528, filed Mar. 22, 2005, 19 pages.

Final Office Action mailed Feb. 1, 2008, for U.S. Appl. No. 10/310,113, filed Dec. 4, 2002, 14 pages.

International Search Report mailed on May 7, 1998, for PCT Application No. PCT/US98/04644, filed on Mar. 10, 1998, three pages.

International Search Report mailed on Jun. 30, 2003, for PCT Application No. PCT/US02/034727, filed on Oct. 29, 2002, three pages.

International Search Report mailed on May 18, 2005, for PCT Application No. PCT/US04/17900, filed on Jun. 4, 2004, two pages.

Lewis, A.P. et al. (1993). "Generation of Humanized Monoclonal Antibodies by 'Best Fit' Framework Selection and Recombinant Polymerase Chain Reaction," *Year Immunol.* 7:110-118.

Medline Encyclopedia definition of "sepsis" located at <http://www.nlm.nih.gov/medlineplus/print/ency/article/000666.htm...>, last visited on Jul. 20, 2007, 3 pages.

Morrow, D.A. et al. (Apr. 2005). "Potent Inhibition of Thrombin with a Monoclonal Antibody Against Tissue Factor (Sunol-cH36): Results of the PROXIMATE-TIMI 27 Trial," *European Heart Journal* 26(7):682-688.

Non-Final Office Action mailed Mar. 11, 2004, for U.S. Appl. No. 09/990,586, filed Nov. 21, 2001, 12 pages.

Non-Final Office Action mailed Sep. 22, 2004, for U.S. Appl. No. 10/293,417, filed Nov. 12, 2002, six pages.

Non-Final Office Action mailed Oct. 21, 2005, for U.S. Appl. No. 10/310,113, filed Dec. 4, 2002, 27 pages.

Non-Final Office Action mailed Mar. 24, 2006, for U.S. Appl. No. 11/087,528, filed Mar. 22, 2005, 13 pages.

Non-Final Office Action mailed Apr. 4, 2007, for U.S. Appl. No. 11/087,528, filed Mar. 22, 2005, 15 pages.

Non-Final Office Action mailed May 11, 2007, for U.S. Appl. No. 10/310,113, filed Dec. 4, 2002, 14 pages.

Non-Final Office Action mailed Feb. 4, 2008, for U.S. Appl. No. 10/764,140, filed Jan. 22, 2004, 12 pages.

Non-Final Office Action mailed Sep. 15, 2008, for U.S. Appl. No. 11/122,622, filed May 5, 2005, 13 pages.

Palmerini, T. et al. (Oct. 19, 2004). "Monocyte-Derived Tissue Factor Contributes to Stent Thrombosis in an In Vitro System," *J. Am. Coll. Cardio.* 44(8):1570-1577.

Portolano, S. et al. (Feb. 1, 1993). "Lack of Promiscuity in Autoantigen-Specific H and L Chain Combinations as Revealed by Human H and L Chain 'Roulette'," *J. Immunology* 150(3):880-887.

Ward, E.S. (Apr. 20, 1992). "Secretion of T Cell Receptor Fragments from Recombinant *Escherichia coli* Cells," *Journal of Molecular Biology* 224(4):885-890.

Welty-Wolf, K.E. et al. (Jan. 2006, e-pub. Aug. 12, 2005). "Blockade of Tissue Factor-Factor X Binding Attenuates Sepsis-Induced Respiratory and Renal Failure," *Am. J. Physiol. Cell. Mol. Physiol.* 290(1, pt. 1):L21-L31.

Written Opinion mailed on Oct. 7, 2004, for PCT Application No. PCT/US02/34727, filed on Oct. 29, 2002, five pages.

* cited by examiner

H36.D2.B7 ANTI-TISSUE FACTOR LIGHT CHAIN VARIABLE REGION

GACATTCAGATGACCCAGTCTCCTGCCTCCCAGTCTGCATCTCTGGGAGAAAGTGTCACCATCACATGC
 D  I  Q  M  T  Q  S  P  A  S  Q  S  A  S  L  G  E  S  V  T  I  T  C

CTGGCAAGTCAGACCATTGATACATGGTTAGCATGGTATCAGCAGAAACCAGGGAAATCTCCTCAGCTC
 L  A  S  Q  T  I  D  T  W  L  A  W  Y  Q  Q  K  P  G  K  S  P  Q  L

CTGATTTATGCTGCCACCAACTTGGCAGATGGGGTCCCATCAAGGTTCAGTGGCAGTGGATCTGGCACA
 L  I  Y  A  A  T  N  L  A  D  G  V  P  S  R  F  S  G  S  G  S  G  T

AAATTTCTTTCAAGATCAGCAGCCTACAGGCTGAAGATTTTGTAAATTATTACTGTCAACAAGTTTAC
 K  F  F  S  R  S  A  A  Y  R  L  K  I  L  *  I  I  T  V  N  K  V  Y

AGTTCTCCATTCACGTTCGGTGCTGGGACCAAGCTGGAGCTGAAA
 S  S  P  F  T  F  G  A  G  T  K  L  E  L  K

FIG. 1A

H36.D2.B7 ANTI-TISSUE FACTOR HEAVY CHAIN VARIABLE REGION

```
GAGATCCAGCTGCAGCAGTCTGGACCTGAGCTGGTGAAGCCTGGGGCTTCAGTGCAGGTATCCTGCAAG
 E  I  Q  L  Q  Q  S  G  P  E  L  V  K  P  G  A  S  V  Q  V  S  C  K

ACTTCTGGTTACTCATTCACTGACTACAACGTGTACTGGGTGAGGCAGAGCCATGGAAAGAGCCTTGAG
 T  S  G  Y  S  F  T  D  Y  N  V  Y  W  V  R  Q  S  H  G  K  S  L  E

TGGATTGGATATATTGATCCTTACAATGGTATTACTATCTACGACCAGAACTTCAAGGGCAAGGCCACA
 W  I  G  Y  I  D  P  Y  N  G  I  T  I  Y  D  Q  N  F  K  G  K  A  T

TTGACTGTTGACAAGTCTTCCACCACAGCCTTCATGCATCTCAACAGCCTGACATCTGACGACTCTGCA
 L  T  V  D  K  S  S  T  T  A  F  M  H  L  N  S  L  T  S  D  D  S  A

GTTTATTTCTGTGCAAGAGATGTGACTACGGCCCTTGACTTCTGGGGCCAAGGCACCACTCTCACAGTC
 V  Y  F  C  A  R  D  V  T  T  A  L  D  F  W  G  Q  G  T  T  L  T  V

TCCTCA
 S  S
```

FIG. 1B

| ANTIBODY | APPARENT $K_1$, M$^{-1}$ | APPARENT $K_1$, M |
|---|---|---|
| BY ELISA | | |
| D2 | $5.2 \times 10^9$ | $1.9 \times 10^{-10}$ |
| I47 | $6.5 \times 10^9$ | $1.5 \times 10^{-10}$ |
| K73 | $9.8 \times 10^9$ | $1.0 \times 10^{-10}$ |
| K80 | $2.3 \times 10^9$ | $4.3 \times 10^{-10}$ |
| L102 | $2.5 \times 10^9$ | $4.0 \times 10^{-10}$ |
| L133 | $1.7 \times 10^9$ | $5.9 \times 10^{-10}$ |
| BY BIACore | | |
| H36 | $3.1 \times 10^{10}$ | $3.2 \times 10^{-11}$ |
| I43 | $2.3 \times 10^9$ | $4.3 \times 10^{-10}$ |
| I47 | $3.2 \times 10^9$ | $3.1 \times 10^{-10}$ |
| L133 | $4.6 \times 10^9$ | $2.2 \times 10^{-10}$ |
| M107 | $1.1 \times 10^9$ | $9.1 \times 10^{-10}$ |

FIG. 2

| ANTIBODY NAME | % INHIBITION ANTIBODY PREINCUBATED WITH TF/VIIa |
|---|---|
| D1 | 0 |
| D1B | 1 |
| H31 | 4 |
| H36 | 95 |
| I43 | 1 |
| J131 | 7 |
| K80 | 0 |
| K82 | 0 |
| K87 | 1 |
| L97B | 7 |
| L101 | 0 |
| L102 | 0 |
| L105 | 0 |
| L133 | 0 |
| M5 | 1 |
| M107 | 34 |

FIG. 3

| ANTIBODY NAME | % INHIBITION TF PREINCUBATED WITH ANTIBODY PRIOR TO ADDITION OF VIIa | % INHIBITION TF PREINCUBATED WITH VIIa PRIOR TO ADDITION OF ANTIBODY |
|---|---|---|
| D1 | 15 | nd |
| D1B | 48 | 12.7 |
| H31 | 64 | 21 |
| H36 | 0 | 0 |
| I43 | 68 | 55 |
| J131 | 38 | 11 |
| K80 | 12 | nd |
| K82 | 0 | nd |
| K87 | 0 | nd |
| L96 | 0 | nd |
| L101 | 38 | 11 |
| L102 | 14 | nd |
| L105 | 4 | nd |
| L133 | 13 | nd |
| M5 | 0 | nd |
| M107 | 0 | nd |

FIG. 4

| [rhTF], nM | [H36.D2], nM | H36.D2/rhTF MOLAR RATIO | CLOTTING TIME (SECONDS) | % INHIBITION OF rhTF FUNCTION |
|---|---|---|---|---|
| 0.0048 | 0<br>1.61<br>3.23 | 0<br>335.4<br>670.8 | 102.3<br>114.3<br>121.3 | 0<br>31.3<br>45.8 |
| 0.023 | 0<br>1.61<br>3.23<br>6.45 | 0<br>70.0<br>140.0<br>280.4 | 77.6<br>85.3<br>91.1<br>99.6 | 0<br>52.2<br>65.2<br>73.9 |
| 0.092 | 0<br>3.23<br>6.45<br>12.90 | 0<br>35.1<br>70.1<br>140.2 | 49.3<br>65.8<br>88.5<br>113.3 | 0<br>65.2<br>90.2<br>95.7 |
| 0.46 | 0<br>6.45<br>12.90<br>32.30 | 0<br>14.0<br>28.0<br>70.2 | 32.6<br>52.7<br>80.2<br>117.9 | 0<br>82.4<br>96.7<br>99.3 |
| 2.30 | 0<br>16.10<br>32.30<br>64.50 | 0<br>7.0<br>14.0<br>28.0 | 23.9<br>47.1<br>95.2<br>115.3 | 0<br>94.4<br>99.7<br>99.9 |
| 11.52 | 0<br>16.10<br>32.30<br>64.50<br>161.30 | 0<br>1.4<br>2.8<br>5.6<br>14.0 | 22.2<br>30.2<br>46.0<br>87.6<br>114.0 | 0<br>93.4<br>98.8<br>99.9<br>100.0 |

FIG. 5

| H36.D2 CONCENTRATION (ng) | % INHIBITION<br>CELLS (TF/FVII) AND H36.D2 PREINCUBATED PRIOR TO FX ADDITION | % INHIBITION<br>FX AND H36.D2 ARE ADDED SIMULTANEOUSLY TO CELLS (TF/FVII) |
|---|---|---|
| 0 | 0 | 0 |
| 50 | 88 | nd |
| 100 | 92 | nd |
| 200 | 97 | nd |
| 800 | nd | 76 |
| 1600 | nd | 78 |
| 3200 | nd | 92 |

FIG. 7

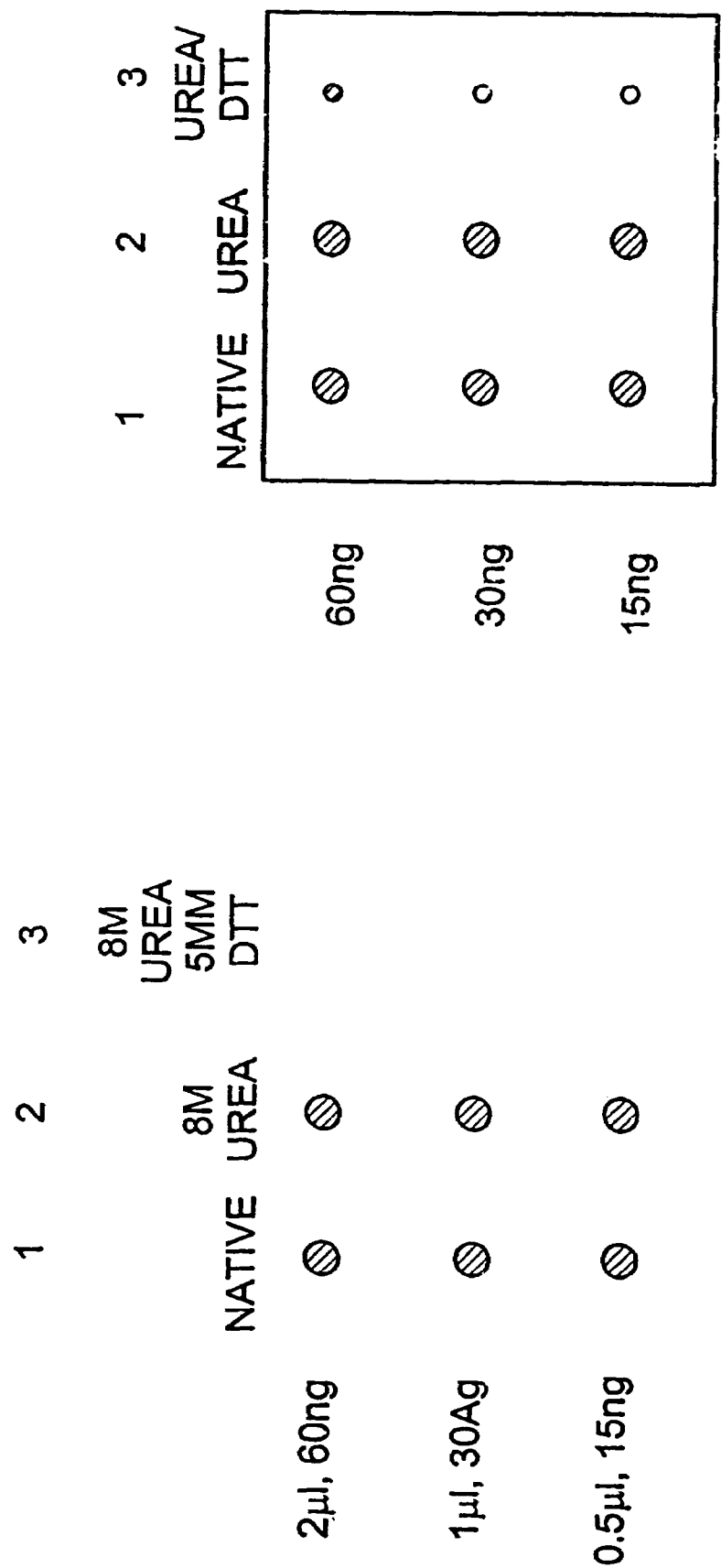

Lung Tumor

Normal Lung

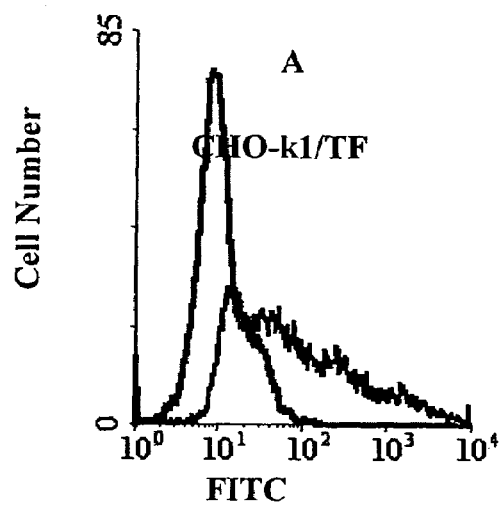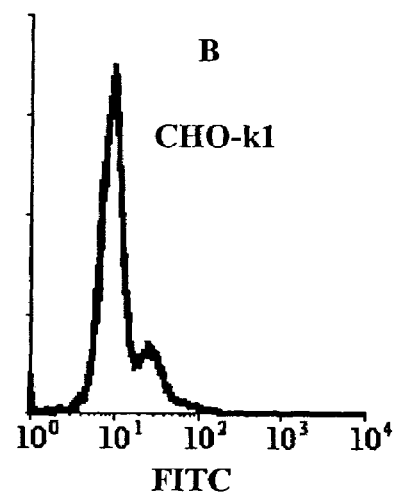
Fig. 12A  Fig. 12B
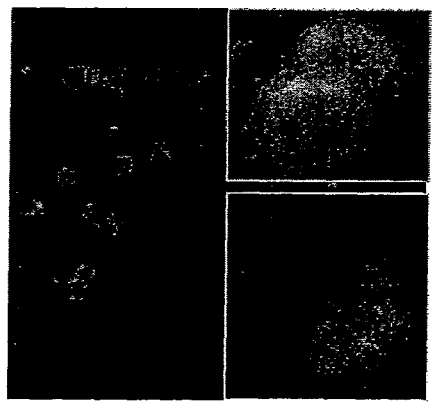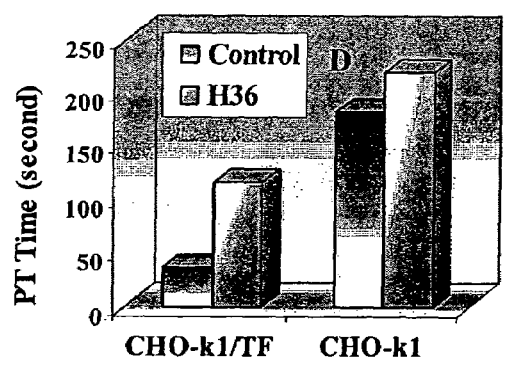
Fig. 12C  Fig. 12D

```
                       SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
         (A) LENGTH: 321 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 1:

GACATTCAGA TGACCCAGTC TCCTGCCTCC CAGTCTGCAT CTCTGGGAGA AAGTGTCACC       60

ATCACATGCC TGGCAAGTCA GACCATTGAT ACATGGTTAG CATGGTATCA GCAGAAACCA      120

GGGAAATCTC CTCAGCTCCT GATTTATGCT GCCACCAACT TGGCAGATGG GGTCCCATCA      180

AGGTTCAGTG GCAGTGGATC TGGCACAAAA TTTTCTTTCA AGATCAGCAG CCTACAGGCT      240

GAAGATTTTG TAAATTATTA CTGTCAACAA GTTTACAGTT CTCCATTCAC GTTCGGTGCT      300

GGGACCAAGC TGGAGCTGAA A                                                321

(2) INFORMATION FOR SEQ ID NO: 2:

(i) SEQUENCE CHARACTERISTICS:
         (A) LENGTH: 107 amino acids
         (B) TYPE: amino acid
         (C) STRANDEDNESS: single
         (D) TOPOLOGY: linear (ii) MOLECULE TYPE: peptide (iii) HYPOTHETICAL: NO
```

(iv) ANTI-SENSE: NO (v) FRAGMENT TYPE: N-terminal (vi) ORIGINAL SOURCE:

(xi) SEQUENCE DESCRIPTION: SEQ ID NO: 2:

```
Asp Ile Gln Met Thr Gln Ser Pro Ala Ser Gln Ser Ala Ser Leu Gly
 1               5                  10                  15

Glu Ser Val Thr Ile Thr Cys Leu Ala Ser Gln Thr Ile Asp Thr Trp
            20                  25                  30

Leu Ala Trp Tyr Gln Gln Lys Pro Gly Lys Ser Pro Gln Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Asn Tyr Tyr Cys Gln Gln Val Tyr Ser Ser Pro Phe
                85                  90                  95

Thr Phe Gly Ala Gly Thr Lys Leu Glu Leu Lys
            100                 105
```

(2) INFORMATION FOR SEQ ID NO: 3:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 3:

```
GAGATCCAGC TGCAGCAGTC TGGACCTGAG CTGGTGAAGC CTGGGGCTTC AGTGCAGGTA      60

TCCTGCAAGA CTTCTGGTTA CTCATTCACT GACTACAACG TGTACTGGGT GAGGCAGAGC     120

CATGGAAAGA GCCTTGAGTG GATTGGATAT ATTGATCCTT ACAATGGTAT TACTATCTAC     180

GACCAGAACT TCAAGGGCAA GGCCACATTG ACTGTTGACA AGTCTTCCAC CACAGCCTTC     240

ATGCATCTCA ACAGCCTGAC ATCTGACGAC TCTGCAGTTT ATTTCTGTGC AAGAGATGTG     300

ACTACGGCCC TTGACTTCTG GGGCCAAGGC ACCACTCTCA CAGTCTCCTC A              351
```

(2) INFORMATION FOR SEQ ID NO: 4:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 4:

Glu Ile Gln Leu Gln Gln Ser Gly Pro Glu Leu Val Lys Pro Gly Ala
1               5                   10                  15

Ser Val Gln Val Ser Cys Lys Thr Xaa Gly Tyr Ser Phe Thr Asp Tyr
            20                  25                  30

Asn Val Tyr Trp Val Arg Gln Ser His Gly Lys Ser Leu Glu Trp Ile
        35                  40                  45

Gly Tyr Ile Asp Pro Tyr Asn Gly Ile Thr Ile Tyr Asp Gln Asn Phe
    50                  55                  60

Lys Gly Lys Ala Thr Leu Thr Val Asp Lys Ser Ser Thr Thr Ala Phe
65                  70                  75                  80

Met His Leu Asn Ser Leu Thr Ser Asp Asp Ser Ala Val Tyr Phe Cys
                85                  90                  95

Ala Arg Asp Val Thr Thr Ala Leu Asp Phe Trp Gly Gln Gly Thr Thr
            100                 105                 110

Leu Thr Val Ser Ser
        115

(2) INFORMATION FOR SEQ ID NO: 5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 5:

Leu Ala Ser Gln Thr Ile Asp
1               5

(2) INFORMATION FOR SEQ ID NO: 6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 6:

Ala Ala Thr Asn Leu Ala Asp
1               5

(2) INFORMATION FOR SEQ ID NO: 7:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 7:

Gln Gln Val Tyr Ser Ser Pro Phe Thr
1               5

(2) INFORMATION FOR SEQ ID NO: 8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 8:

Thr Asp Tyr Asn Val Tyr
1               5

(2) INFORMATION FOR SEQ ID NO: 9:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 9:

Tyr Ile Asp Pro Tyr Asn Gly Ile Thr Ile Tyr Asp Gln Asn Phe Lys
1               5                   10                  15
Gly (2) INFORMATION FOR SEQ ID NO: 10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 10:

Asp Val Thr Thr Ala Leu Asp Phe
 1               5

(2) INFORMATION FOR SEQ ID NO: 11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

CTGGCAAGTC AGACCATTGA T                                              21

(2) INFORMATION FOR SEQ ID NO: 12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

GCTGCCACCA ACTTGGCAGA T                                              21

(2) INFORMATION FOR SEQ ID NO: 13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

CAACAAGTTT ACAGTTCTCC ATTCACGT                                          28

(2) INFORMATION FOR SEQ ID NO: 14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

ACTGACTACA ACGTGTAC                                                     18

(2) INFORMATION FOR SEQ ID NO: 15:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 15:

TATATTGATC CTTACAATGG TATTACTATC TACGACCAGA ACTTCAAGGG C                 51

(2) INFORMATION FOR SEQ ID NO: 16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

GATGTGACTA CGGCCCTTGA CTTC                                              24

(2) INFORMATION FOR SEQ ID NO: 17:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

GCACCTCCAG ATGTTAACTG CTC                                                   23

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

GAARTAVCCC TTGACCAGGC                                                       20

(2) INFORMATION FOR SEQ ID NO: 19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

GGAGGCGGCG GTTCTGACAT TGTGMTGWCM CARTC                                      35

(2) INFORMATION FOR SEQ ID NO: 20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

ATTTCAGGCC CAGCCGGCCA TGGCCGARGT YCARCTKCAR CARYC                45

(2) INFORMATION FOR SEQ ID NO: 21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

CCCGGGCCAC CATGKCCCCW RCTCAGYTYC TKG                              33

(2) INFORMATION FOR SEQ ID NO: 22:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

CCCGGGCCAC CATGGRATGS AGCTGKGTMA TSCTC                            35

(2) INFORMATION FOR SEQ ID NO: 23:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

ATATACTCGC GACAGCTACA GGTGTCCACT CCGAGATCCA GCTGCAGCAG TC         52

(2) INFORMATION FOR SEQ ID NO: 24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

GACCTGAATT CTAAGGAGAC TGTGAGAGTG G          31

(2) INFORMATION FOR SEQ ID NO: 25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

TTAATTGATA TCCAGATGAC CCAGTCTCC          29

(2) INFORMATION FOR SEQ ID NO: 26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

TAATCGTTCG AAAAGTGTAC TTACGTTTCA GCTCCAGCTT GGTCC          45

ANTIBODIES FOR INHIBITING BLOOD COAGULATION AND METHODS OF USE THEREOF

CROSS-REFERENCE TO RELATED APPLICATIONS

The present application is a continuation-in-part of U.S. Ser. No. 10/293,417 as filed on Nov. 12, 2002 (now abandoned), which application is a continuation of U.S. Ser. No. 09/293,854 as filed on Apr. 16, 1999 (now U.S. Pat. No. 6,555,319), which application is a continuation of U.S. Ser. No. 08/814,806 (now U.S. Pat. No. 5,986,065) as filed on Mar. 10, 1997. The disclosures of the U.S. Ser. No. 10/293,417 and U.S. Pat. Nos. 6,555,319 and 5,986,065 are incorporated herein by reference.

BACKGROUND OF THE INVENTION

1. Field of the Invention

The present invention relates to novel antibodies and methods of using the antibodies to inhibit blood coagulation. In particular, the invention relates to novel antibodies that can specifically bind native human tissue factor with high affinity. The antibodies of the invention are useful for a variety of applications, particularly for reducing blood coagulation in vivo.

2. Background

Blood clotting assists homeostasis by minimizing blood loss. Generally, blood clotting requires vessel damage, platelet aggregation, coagulation factors and inhibition of fibrinolysis. The coagulation factors act through a cascade that relates the vessel damage to formation of a blood clot (see generally L. Stryer, *Biochemistry,* 3rd Ed, W.H. Freeman Co., New York; and A. G. Gilman et al., *The Pharmacological Basis of Therapeutics,* 8th Edition, McGraw Hill Inc., New York, pp. 1311-1331).

There is general agreement that factor X (FX) activation to factor Xa (FXa) is a critical step in the blood coagulation process. Generally, FX is converted to FXa by binding a catalytically active complex that includes "tissue factor" (TF). TF is a controllably-expressed cell membrane protein that binds factor VII/VIIa to produce the catalytically active complex (TF:VIIa). A blood clot follows FXa-mediated activation of prothrombin. Blood clotting can be minimized by inactivation of TF to non-native forms which cannot optimally produce the TF:VIIa complex. Excessive formation of FXa is believed to contribute to various thromboses including restenosis.

Thrombosis may be associated with invasive medical procedures such as cardiac surgery (e.g. angioplasty), abdominothoracic surgery, arterial surgery, deployment of an implementation (e.g., a stent or catheter), or endarterectomy. Further, thrombosis may accompany various thromboembolic disorders and coagulopathies such as a pulmonary embolism (e.g., atrial fibrillation with embolization) and disseminated intravascular coagulation, respectively. Manipulation of body fluids can also result in an undesirable thrombus, particularly in blood transfusions or fluid sampling, as well as procedures involving extracorporeal circulation (e.g., cardiopulmonary bypass surgery) and dialysis.

Anti-coagulants are frequently used to alleviate or avoid blood clots associated with thrombosis. Blood clotting often can be minimized or eliminated by administering a suitable anti-coagulant or mixture thereof, including one or more of a coumarin derivative (e.g., warfin and dicumarol) or a charged polymer (e.g., heparin, hirudin or hirulog). See e.g., Gilman et al., supra, R. J. Beigering et al., *Ann. Hemathol.,* 72:177 (1996); J. D. Willerson, *Circulation,* 94:866 (1996).

However, use of anti-coagulants is often associated with side effects such as hemorrhaging, re-occlusion, "white-clot" syndrome, irritation, birth defects, thrombocytopenia and hepatic dysfunction. Long-term administration of anti-coagulants can particularly increase risk of life-threatening illness (see e.g., Gilman et al., supra).

Certain antibodies with anti-platelet activity have also been used to alleviate various thromboses. For example, ReoPro™ is a therapeutic antibody that is routinely administered to alleviate various thromboembolic disorders such as those arising from angioplasty, myocardial infarction, unstable angina and coronary artery stenoses. Additionally, ReoPro™ can be used as a prophylactic to reduce the risk of myocardial infarction and angina (J. T. Willerson, *Circulation,* 94:866 (1996); M. L. Simmons et al., *Circulation,* 89:596 (1994)).

Certain anti-coagulant antibodies are also known. Particularly, certain TF-binding antibodies have been reported to inhibit blood coagulation, presumably by interfering with assembly of a catalytically active TF:VIIa complex (see e.g., Jeske et al., *SEM in THROM. and HEMO,* 22:213 (1996); Ragni et al., *Circulation,* 93:1913 (1996); European Patent No. 0 420 937 B1; W. Ruf et al., *Throm. Haemosp.,* 66:529 (1991); M. M. Fiorie et al., *Blood,* 8:3127 (1992)).

However, current TF-binding antibodies exhibit significant disadvantages which can minimize their suitably as anti-coagulants. For example, current TF-binding antibodies do not exhibit sufficient binding affinity for optimal anti-coagulant activity. Accordingly, for many thrombotic conditions, to compensate for such ineffective binding affinities, unacceptably high antibody levels must be administered to minimize blood coagulation. Further, current TF-binding antibodies do not effectively discriminate between native TF and non-native forms of TF, i.e. the current antibodies do not exhibit sufficient binding specificity. Still further, current TF-binding antibodies can not prevent FX from binding to TF and/or TF:VIIa complex.

It would thus be desirable to have an anti-coagulant antibody that binds native human TF with high affinity and selectivity to thereby inhibit undesired blood coagulation and the formation of blood clots. It would be further desirable to have such an anti-coagulant antibody that prevents the binding of Factor X to TF/VIIa complex.

SUMMARY OF THE INVENTION

We have now discovered antibodies that provide superior anti-coagulant activity by binding native human TF with high affinity and specificity. Antibodies of the invention can effectively inhibit blood coagulation in vivo. Antibodies of the invention can bind native human TF, either alone or present in a TF:VIIa complex, effectively preventing factor X binding to TF or that complex, and thereby reducing blood coagulation.

Preferred antibodies of the invention are monoclonal and specifically bind a conformational epitope predominant to native human TF, which epitope provides an unexpectedly strong antibody binding site. Indeed, preferred antibodies of the invention bind to native human TF at least about 5 times greater, more typically at least about ten times greater than the binding affinity exhibited by prior anti-coagulant antibodies. Additionally, preferred antibodies of the invention are selective for native human TF, and do not substantially bind non-native or denatured TF. H36.D2.B7 (secreted by hybridoma ATCC HB-12255) is an especially preferred antibody of the invention.

Preferred antibodies of the invention bind TF so that FX does not effectively bind to the TF/factor VIIa complex whereby FX is not effectively converted to its activated form (FXa). Preferred antibodies of the invention can inhibit TF function by effectively blocking FX binding or access to TF molecules. See, for instance, the results of Example 3 which follows.

Preferred antibodies of the invention also do not significantly inhibit the interaction or binding between TF and factor VIIa, or inhibit activity of a TF:factor VIIa complex with respect to materials other than FX. See, for instance, the results of Example 4 which follows.

The invention also provides nucleic acids that encode antibodies of the invention. Nucleic acid and amino acid sequences (SEQ ID:NOS 1-4) of variable regions of H36.D2.B7 are set forth in FIGS. IA and IB of the drawings.

In preferred aspects, the invention provides methods for inhibiting blood coagulation and blood clot formation, and methods for reducing human TF levels.

In general, antibodies of the invention will be useful to modulate virtually any biological response mediated by FX binding to TF or the TF: VIIa complex, including blood coagulation as discussed above, inflammation and other disorders.

Antibodies of the invention are particularly useful to alleviate various thromboses, particularly to prevent or inhibit restenosis, or other thromboses following an invasive medical procedure such as arterial or cardiac surgery (e.g., angioplasty). Antibodies of the invention also can be employed to reduce or even effectively eliminate blood coagulation arising from use of medical implementation (e.g., a catheter, stent or other medical device). Preferred antibodies of the invention will be compatible with many anti-coagulant, anti-platelet and thrombolytic compositions, thereby allowing administration in a cocktail format to boost or prolong inhibition of blood coagulation.

Antibodies of the invention also can be employed as an anti-coagulant in extracorporeal circulation of a mammal, particularly a human subject. In such methods, one or more antibodies of the invention is administered to the mammal in an amount sufficient to inhibit blood coagulation prior to or during extracorporeal circulation such as may be occur with cardiopulmonary bypass surgery, organ transplant surgery or other prolonged surgeries.

Antibodies of the invention also can be used as a carrier for drugs, particularly pharmaceuticals targeted for interaction with a blood clot such as strepokinase, tissue plasminogen activator (t-PA) or urokinase. Similarly, antibodies of the invention can be used as a cytotoxic agent by conjugating a suitable toxin to the antibody. Conjugates of antibodies of the invention also can be used to reduce tissue factor levels in a mammal, particularly a human, by administering to the mammal an effective amount of an antibody of the invention which is covalently linked a cell toxin or an effector molecule to provide complement-fixing ability and antibody-dependent cell-mediated cytotoxicity, whereby the antibody conjugate contacts cells expressing tissue factor to thereby reduce tissue factor levels in the mammal.

Antibodies of the invention also can be employed in in vivo diagnostic methods including in vivo diagnostic imaging of native human TF.

Antibodies of the invention also can be used in in vitro assays to detect native TF in a biological sample including a body fluid (e.g., plasma or serum) or tissue (e.g., a biopsy sample). More particularly, various heterogeneous and homogeneous immunoassays can be employed in a competitive or non-competitive format to detect the presence and preferably an amount of native TF in the biological sample.

Such assays of the invention are highly useful to determine the presence or likelihood of a patient having a blood coagulation or a blood clot. That is, blood coagulation is usually accompanied by TF expression on cells surfaces such as cells lining the vasculature. In the absence of blood coagulation, TF is not usually expressed. Thus, the detection of TF in a body fluid sample by an assay of the invention will be indicative of blood coagulation.

Antibodies of the invention also can be used to prepare substantially pure native TF, particularly native human TF, from a biological sample. Antibodies of the invention also can be used for detecting and purifying cells which express native TF.

Antibodies of the invention also can be employed as a component of a diagnostic kit, e.g. for detecting and preferably quantitating native TF in a biological sample. Other aspects of the invention are discussed infra.

BRIEF DESCRIPTION OF THE DRAWINGS

FIGS. 1A and 1B shows the nucleic acid (SEQ ID NOS:1 and 3) and amino acid (SEQ ID NOS:2 and 4) sequences of light chain and heavy chain variable regions of H36.D2.B7 with hypervariable regions (CDRs or Complementarity Determining Regions) underlined (single underline for nucleic acid sequences and double underline for amino acid sequences).

FIG. 2 shows association ($K_a$) and disassociation ($K_d$) constants of anti-tissue factor antibodies as determined by ELISA or BIACore analysis.

FIG. 3 shows inhibition of TF:VIIa complex mediated FX activation by pre-incubation with anti-tissue factor antibodies.

FIG. 4 shows inhibition of TF/VIIa activity toward the FVIIa-specific substrate S-2288 by anti-tissue factor antibodies.

FIG. 5 shows the capacity of the H36 antibody to increase prothrombin time (PT) in a TF-initiated coagulation assay.

FIG. 6A: H36.D2 was pre-incubated with the FT:VIIa complex prior to adding FX. FIG. 6B: H36.D2, TF:VIIa and FX were added simultaneously.

FIG. 7 shows inhibition of TF:VIIa activity by the H36.D2 antibody in a J-82 cell activation assay.

FIGS. 8A and 8B are representations of dot blots showing that the H36.D2 antibody binds a conformational epitope on rhTF. Lane 1-native rHTF, Lane 2-native rhTF treated with 8M urea, Lane 3-native rHTF treated with 8M urea and 5 mM DTT. In FIG. 8A, the blot was exposed for approximately 40 seconds, whereas in FIG. 8B, the blot was exposed for 120 seconds.

FIG. 9A is a photograph showing detection of TF antigen on cell surface of tumor MDA-MB 435/TF cells. FIGS. 9B-C are graphical results (FIGS. 9B, C) of immunofluorescent detection of TF antigen on surface of the same cells.

FIGS. 12A-B are graphs showing detection of TF antigen and its activity on CHO-k1/TF and CHO-k1 cells. FIG. 12C is a photomicrograph showing immunofluorescent staining using anti-tissue factor antibody H36. FIG. 12D is a photomicrograph showing prothrombin time (PT) using the same antibody.

DETAILED DESCRIPTION OF THE INVENTION

Figure 6A:
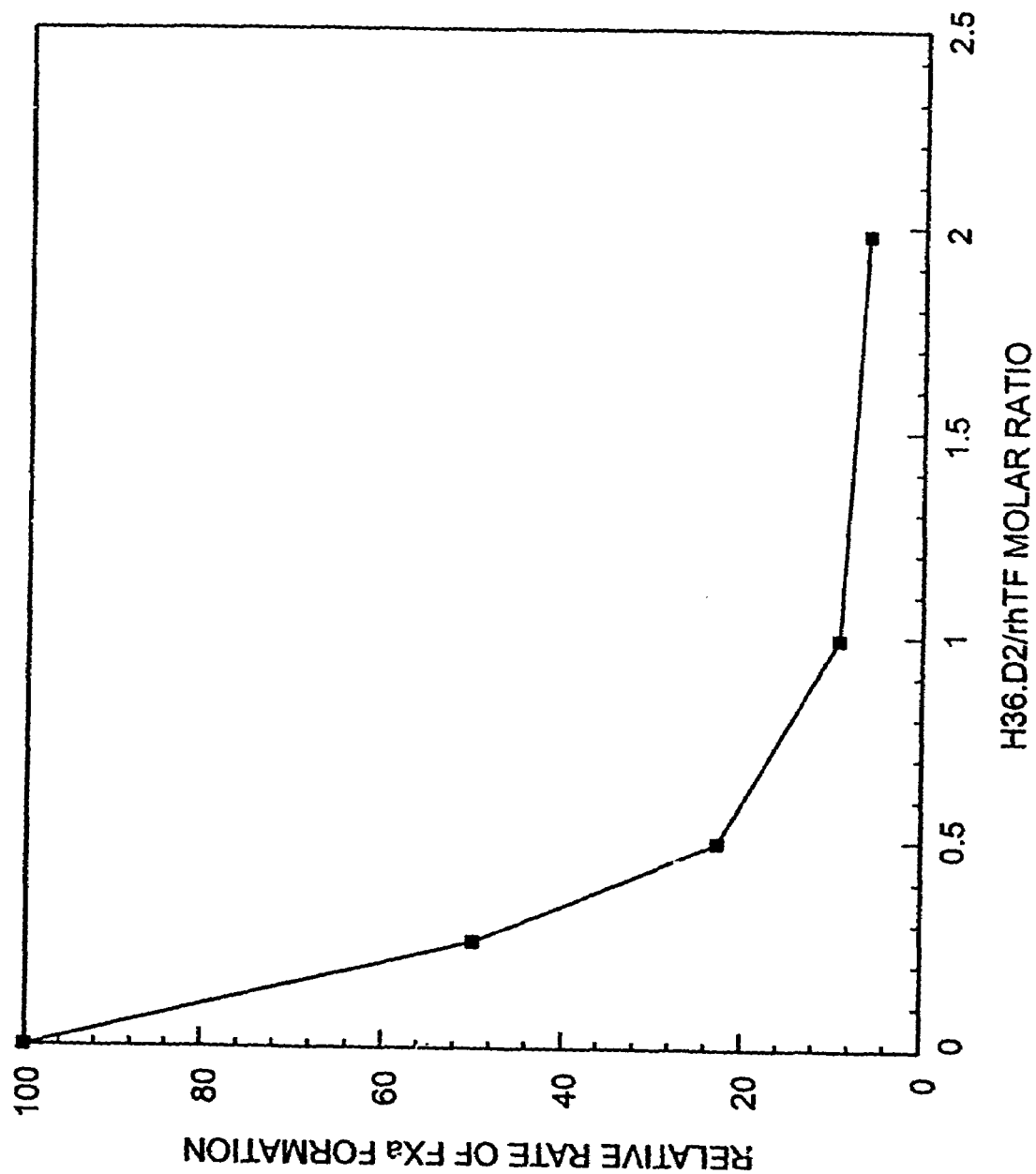
FIGS. 6A and 6B graphically show the relationship between FXa formation and molar ratio of the H36.D2 antibody and rHTF.

As discussed above, preferred antibodies of the invention exhibit substantial affinity for native human TF. In particular, preferred antibodies of the invention exhibit an association constant ($K_a$, $M^{-1}$) for native human TF of at least about $1 \times 10^8$ as determined by surface plasmon analysis (particularly, BIACore analysis in accordance with the procedures of Example 1 which follows), more preferably at least about $5 \times 10^8$ as determined by surface plasmon analysis, still more preferably a $K_a$ ($K_a$, $M^{-1}$) for native human TF of at least about $1 \times 10^{10}$ as determined by surface plasmon analysis. Such substantial binding affinity of antibodies of the invention contrast sharply from much lower binding affinities of previously reported antibodies.

In this regard, a quite low of effective concentration of an antibody of the invention can be employed, e.g. a relatively low concentration of antibody can be employed to inhibit TF function as desired (e.g. at least about 95, 98 or 99 percent inhibition) in an in vitro assay such as described in Example 3 which follows.

The preferred antibodies are also highly specific for native human TF, and preferably do not substantially bind with non-native TF. Preferred antibodies do not substantially bind non-native TF or other immunologically unrelated molecules as determined, e.g. by standard dot blot assay (e.g. no or essentially no binding to non-native TF visually detected by such dot blot assay). References herein to "non-native TF" mean a naturally-occurring or recombinant human TF that has been treated with a choatropic agent so that the TF is denatured. Typical choatropic agents include a detergent (e.g. SDS), urea combined with dithiothreotol or β-mercaptoethanol; guanidine hydrochloride and the like. The H36, H36.D2 or H36.D2.B7 antibody does not substantially bind to such non-native TF. See, for instance, the results of Example 8 which follows and is a dot blot assay.

As discussed above, preferred antibodies of the invention also bind with TF so that FX does not effectively bind to the TF/factor VIIa complex whereby FX is not effectively converted to its activated form (FXa). Particularly preferred antibodies of the invention exhibit will strongly inhibit FX activity to a TF/factor VIIa complex, e.g. an inhibition of at least about 50%, more preferably at least about 80%, and even more preferably at least about 90% or 95%, even at low TF concentrations such as less than about 1.0 nM TF, or even less than about 0.20 nM or 0.10 nM TF, as determined by a standard in vitro binding assay such as that of Example 3 which follows and includes contacting FX with a TF:factor VIIa complex both in the presence (i.e. experimental sample) and absence (i.e. control sample) of an antibody of the invention and determining the percent difference of conversion of FX to FXa between the experimental and control samples.

Antibodies of the invention are preferably substantially pure when used in the disclosed methods and assays. References to an antibody being "substantially pure" mean an antibody or protein which has been separated from components which naturally accompany it. For example, by using standard immunoaffinity or protein A affinity purification techniques, an antibody of the invention can be purified from a hybridoma culture by using native TF as an antigen or protein A resin. Similarly, native TF can be obtained in substantially pure form by using an antibody of the invention with standard immunoaffinity purification techniques. Particularly, an antibody or protein is substantially pure when at least 50% of the total protein (weight % of total protein in a given sample) is an antibody or protein of the invention. Preferably the antibody or protein is at least 60 weight % of the total protein, more preferably at least 75 weight %, even more preferably at least 90 weight %, and most preferably at least 98 weight % of the total material. Purity can be readily assayed by known methods such as SDS (PAGE) gel electrophoresis, column chromatography (e.g., affinity chromatography) or HPLC analysis.

The nucleic acid (SEQ ID NOS: 1 and 3) and amino acid (SEQ ID NOS: 2 and 4) sequences of a preferred antibody of the invention (H36.D2.B7) are shown in FIGS. 1A and 1B of the drawings. SEQ ID NOS. 1 and 2 are the nucleic acid and amino acid respectively of the light chain variable region, and SEQ ID NOS. 3 and 4 are the nucleic acid and amino acid respectively of the heavy chain variable region, with hypervariable regions (CDRs or Complementarity Determining Regions) underlined in all of those sequences.

Additional preferred antibodies of the invention will have substantial sequence identity to either one or both of the light chain or heavy sequences shown in FIGS. 1A and 1B. More particularly, preferred antibodies include those that have at least about 70 percent homology (sequence identity) to SEQ ID NOS. 2 and/or 4, more preferably about 80 percent or more homology to SEQ ID NOS. 2 and/or 4, still more preferably about 85, 90 or 95 percent or more homology to SEQ ID NOS. 2 and/or 4.

Preferred antibodies of the invention will have high sequence identity to hypervariable regions (shown with double underlining in FIGS. 1A and 1B) of SEQ ID NOS. 2 and 4). Especially preferred antibodies of the invention will have one, two or three hypervariable regions of a light chain variable region that have high sequence identity (at least 90% or 95% sequence identity) to or be the same as one, two or three of the corresponding hypervariable regions of the light chain variable region of H36.D2.B7 (those hypervariable regions shown with underlining in FIG. 1A and are the following: 1) LASQTID (SEQ ID NO:5); 2) AATNLAD (SEQ ID NO:6); and 3) QQVYSSPFT (SEQ ID NO:7)).

Especially preferred antibodies of the invention also will have one, two or three hypervariable regions of a heavy chain variable region that have high sequence identity (at least 90% or 95% sequence identity) to or be the same as one, two or three of the corresponding hypervariable regions of the heavy chain variable region of H36.D2.B7 (those hypervariable regions shown with underlining in FIG. 1B and are the following: 1) TDYNVY (SEQ ID NO:8); 2) YIDPYNGITIY-DQNFKG (SEQ ID NO:9); and 3) DVTTALDF (SEQ ID NO:10).

Nucleic acids of the invention preferably are of a length sufficient (preferably at least about 100, 200 or 250 base pairs) to bind to the sequence of SEQ ID NO:1 and/or SEQ ID NO:3 under the following moderately stringent conditions (referred to herein as "normal stringency" conditions): use of a hybridization buffer comprising 20% formamide in 0.8M saline/0.08M sodium citrate (SSC) buffer at a temperature of 37° C. and remaining bound when subject to washing once with that SSC buffer at 37° C.

More preferably, nucleic acids of the invention (preferably at least about 100, 200 or 250 base pairs) will bind to the sequence of SEQ ID NO: 1 and/or SEQ ID NO:3 under the following highly stringent conditions (referred to herein as "high stringency" conditions): use of a hybridization buffer comprising 20% formamide in 0.9M saline/0.09M sodium citrate (SSC) buffer at a temperature of 42° C. and remaining bound when subject to washing twice with that SSC buffer at 42° C.

Nucleic acids of the invention preferably comprise at least 20 base pairs, more preferably at least about 50 base pairs, and still more preferably a nucleic acid of the invention comprises at least about 100, 200, 250 or 300 base pairs.

Generally preferred nucleic acids of the invention will express an antibody of the invention that exhibits the preferred binding affinities and other properties as disclosed herein.

Preferred nucleic acids of the invention also will have substantial sequence identity to either one or both of the light chain or heavy sequences shown in FIGS. 1A and 1B. More particularly, preferred nucleic acids will comprise a sequence that has at least about 70 percent homology (sequence identity) to SEQ ID NOS. 1 and/or 3, more preferably about 80 percent or more homology to SEQ ID NOS. 1 and/or 3, still more preferably about 85, 90 or 95 percent or more homology to SEQ ID NOS. 1 and/or 3.

Particularly preferred nucleic acid sequences of the invention will have high sequence identity to hypervariable regions (shown with underlining in FIGS. 1A and 1B) of SEQ ID NOS. 1 and 3). Especially preferred nucleic acids include those that code for an antibody light chain variable region and have one, two or three sequences that code for hypervariable regions and have high sequence identity (at least 90% or 95% sequence identity) to or be the same as one, two or three of the sequences coding for corresponding hypervariable regions of H36.D2.B7 (those hypervariable regions shown with underlining in FIG. 1A and are the following: 1) CTGGCAAGTCAGACCATTGAT (SEQ ID NO: 11); 2) GCTGCCACCAACTTGGCAGAT (SEQ ID NO: 12); and 3) CAACAAGTTTACAGTTCT CCATTCACGT (SEQ ID NO: 13)).

Especially preferred nucleic acids also code for an antibody heavy chain variable region and have one, two or three sequences that code for hypervariable regions and have high sequence identity (at least 90% or 95% sequence identity) to or be the same as one, two or three of the sequences coding for corresponding hypervariable regions of H36.D2.B7 (those hypervariable regions shown with underlining in FIG. 1B and are the following: 1) ACTGACTACAACGTGTAC (SEQ ID NO: 14); 2) TATATTGAT CCTTACAATGGTATTACTATCTACGACCAGAACTTCAAGGGC (SEQ ID NO: 15); and 3) GATGTGACTACGGCCCTTGACTTC (SEQ ID NO: 16)).

Nucleic acids of the invention are isolated, usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

Antibodies of the invention can be prepared by techniques generally known in the art, and are typically generated to a purified sample of native TF, typically native human TF, preferably purified recombinant human tissue factor (rhTF). Truncated recombinant human tissue factor or "rhTF" (composed of 243 amino acids and lacking the cytoplasmic domain) is particularly preferred to generate antibodies of the invention. The antibodies also can be generated from an immunogenic peptide that comprises one or more epitopes of native TF that are not exhibited by non-native TF. References herein to "native TF" include such TF samples, including such rhTF. As discussed above, monoclonal antibodies are generally preferred, although polyclonal antibodies also can be employed.

More particularly, antibodies can be prepared by immunizing a mammal with a purified sample of native human TF, or an immunogenic peptide as discussed above, alone or complexed with a carrier. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection. The optimal immunizing interval, immunizing dose, etc. can vary within relatively wide ranges and can be determined empirically based on this disclosure. Typical procedures involve injection of the antigen several times over a number of months. Antibodies are collected from serum of the immunized animal by standard techniques and screened to find antibodies specific for native human TF. Monoclonal antibodies can be produced in cells which produce antibodies and those cells used to generate monoclonal antibodies by using standard fusion techniques for forming hybridoma cells. See G. Kohler, et al., *Nature*, 256:456 (1975). Typically this involves fusing an antibody producing cell with an immortal cell line such as a myeloma cell to produce the hybrid cell. Alternatively, monoclonal antibodies can be produced from cells by the method of Huse, et al., *Science,* 256:1275 (1989).

One suitable protocol provides for intraperitoneal immunization of a mouse with a composition comprising purified rhTF complex conducted over a period of about two to seven months. Spleen cells then can be removed from the immunized mouse. Sera from the immunized mouse is assayed for titers of antibodies specific for rhTF prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT) or thymidine kinase deficiency (TK). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. See G. Kohler, et al., *Nature*, supra. The thus cloned hybridoma is grown in a culture medium, e.g. RPMI-1640. See G. E. More, et al., *Journal of American Medical Association,* 199:549 (1967). Hybridomas, grown after the fusion procedure, are screened such as by radioimmunoassay or enzyme immunoassay for secretion of antibodies that bind specifically to the purified rhTF, e.g. antibodies are selected that bind to the purified rhTF, but not to non-native TF. Preferably an ELISA is employed for the screen. Hybridomas that show positive results upon such screening can be expanded and cloned by limiting dilution method. Further screens are preferably performed to select antibodies that can bind to rhTF in solution as well as in a human fluid sample. The isolated antibodies can be further purified by any suitable immunological technique including affinity chromatography. A hybridoma culture producing the particular preferred H36.D2.B7 antibody has been deposited pursuant to the Budapest Treaty with the American Type Culture Collection (ATCC) at 12301 Parklawn Drive, Rockville, Md., 10852. The hybridoma culture was deposited with the ATCC on Jan. 8, 1997 and was assigned Accession Number ATCC HB-12255.

For human therapeutic applications, it may be desirable to produce chimeric antibody derivatives, e.g. antibody molecules that combine a non-human animal variable region and a human constant region, to thereby render the antibodies less immunogenic in a human subject than the corresponding non-chimeric antibody. A variety of types of such chimeric antibodies can be prepared, including e.g. by producing human variable region chimeras, in which parts of the variable regions, especially conserved regions of the antigen-binding domain, are of human origin and only the hypervariable regions are of non-human origin. See also discussions of humanized chimeric antibodies and methods of producing same in S. L. Morrison, *Science*, 229:1202-1207 (1985); Oi et al., *BioTechniques*, 4:214 (1986); Teng et al., *Proc. Natl. Acad. Sci. U.S.A.*, 80:7308-7312 (1983); Kozbor et al., *Immunology Today*, 4:7279 (9183); Olsson et al., *Meth. Enzymol.*, 9:3-16 (1982). Additionally, transgenic mice can be employed. For example, transgenic mice carrying human antibody repertoires have been created which can be immunized with native human TF. Splenocytes from such immunized transgenic mice can then be used to create hybridomas that secrete human monoclonal antibodies that specifically react with native human TF as described above. See N. Lonberg et al., Nature, 368:856-859 (1994); L. L. Green et al., Nature Genet., 7:13-21 (1994); S. L. Morrison, *Proc. Natl. Acad. Sci. U.S.A.*, 81:6851-6855 (1994).

Nucleic acids of antibodies of the invention also can be prepared by polymerase chain reaction (see primers disclosed in Example 1 which follows). See generally, Sambrook et al., Molecular Cloning (2d ed. 1989). Such nucleic acids also can be synthesized by known methods, e.g. the phosphate triester method (see Oligonucleotide Synthesis, IRL Press (M. J. Gait, ed., 1984)), or by using a commercially available automated oligonucleotide synthesizer. Such a prepared nucleic acid of the invention can be employed to express an antibody of the invention by known techniques. For example, a nucleic acid coding for an antibody of the invention can be incorporated into a suitable vector by known methods such as by use of restriction enzymes to make cuts in the vector for insertion of the construct followed by ligation. The vector containing the inserted nucleic acid sequence, suitably operably linked to a promoter sequence, is then introduced into host cells for expression. See, generally, Sambrook et al., supra. Selection of suitable vectors can be made empirically based on factors relating to the cloning protocol. For example, the vector should be compatible with, and have the proper replicon for the host cell that is employed. Further, the vector must be able to accommodate the inserted nucleic acid sequence. Suitable host cells will include a wide variety of eukaryotic or prokaryotic cells such as *E. coli* and the like.

The molecular weight of the antibodies of the invention will vary depending on several factors such as the intended use and whether the antibody includes a conjugated or recombinantly fused toxin, pharmaceutical, or detectable label or the like. In general, an antibody of the invention will have a molecular weight of between approximately 20 to 150 kDa. Such molecular weights can be readily are determined by molecular sizing methods such as SDS-PAGE gel electrophoresis followed by protein staining or Western blot analysis.

"Antibody of the invention" or other similar term refers to whole immunoglobulin as well immunologically active fragments which bind native TF. The immunoglobulins and immunologically active fragments thereof include an antibody binding site (i.e., peritope capable of specifically binding native human TF). Exemplary antibody fragments include, for example, Fab, F(v), Fab', F(ab')$_2$ fragments, "half molecules" derived by reducing the disulfide bonds of immunoglobulins, single chain immunoglobulins, or other suitable antigen binding fragments (see e.g., Bird et al., *Science*, pp. 242-424 (1988); Huston et al., *PNAS*, (USA), 85:5879 (1988); Webber et al., *Mol. Immunol.*, 32:249 (1995)). The antibody or immunologically active fragment thereof may be of animal (e.g., a rodent such as a mouse or a rat), or chimeric form (see Morrison et al., PNAS, 81:6851 (1984); Jones et al., *Nature*, pp. 321, 522 (1986)). Single chain antibodies of the invention can be preferred.

Similarly, a "nucleic acid of the invention" refers to a sequence which can be expressed to provide an antibody of the invention as such term is specified to mean immediately above.

As discussed above, antibodies of the invention can be administered to a mammal, preferably a primate such as a human, to prevent or reduce thromboses such as restenosis, typically in a composition including one or more pharmaceutically acceptable non-toxic carriers such as sterile water or saline, glycols such as polyethylene glycol, oils of vegetable origin, and the like. In particular, biocompatible, biodegradable lactide polymer, lactide glycolide copolymer or polyoxyethylene, polyoxypropylene copolymers may be useful excipients to control the release of the antibody-containing compositions described herein. Other potentially useful administration systems include ethylene vinyl acetate copolymer particles, osmotic pumps, and implantable infusion systems and liposomes. Generally, an anti-coagulant composition of the invention will be in the form of a solution or suspension, and will preferably include approximately 0.01% to 10% (w/w) of the antibody of the present invention, preferably approximately 0.01% to 5% (w/w) of the antibody. The antibody can be administered as a sole active ingredient in the composition, or as a cocktail including one or more other anti-coagulant (e.g., heparin, hirudin, or hirulog), anti-platelet (e.g., ReoPro), or thrombolytic agents (e.g., tissue plasminogen activator, strepokinase and urokinase). Additionally, antibodies of the invention can be administered prior to, or after administration of one or more suitable anti-coagulant, anti-platelet or thrombolytic agents to boost or prolong desired anti-coagulation activity.

As also discussed above, antibodies of the invention can be employed to reduce potential blood coagulation arising from use of medical implementation, e.g. an indwelling device such as a catheter, stent, etc. In one preferred method, the implementation can be treated with an antibody of the invention (e.g., as a 1 mg/ml saline solution) prior to contact with a body fluid. Alternatively, or in addition, an antibody of the invention can be combined with the body fluid in an amount sufficient to minimize blood clotting.

Therapeutic anti-coagulant compositions according to the invention are suitable for use in parenteral or intravenous administration, particularly in the form of liquid solutions. Such compositions may be conveniently administered in unit dose and may be prepared in accordance with methods known in the pharmaceutical art. See *Remington's Pharmaceutical Sciences*, (Mack Publishing Co., Easton Pa., (1980)). By the term "unit dose" is meant a therapeutic composition of the present invention employed in a physically discrete unit suitable as unitary dosages for a primate such as a human, each unit containing a pre-determined quantity of active material calculated to produce the desired therapeutic effect in association with the required diluent or carrier. The unit dose will depend on a variety of factors including the type and severity of thrombosis to be treated, capacity of the subject's blood coagulation system to utilize the antibody, and degree of inhibition or neutralization of FX activation desired. Precise amounts of the antibody to be administered typically will be guided by judgement of the practitioner, however, the unit dose will generally depend on the route of administration and be in the range of 10 ng/kg body weight to 50 mg/kg body weight per day, more typically in the range of 100 ng/kg body weight to about 10 mg/kg body weight per day. Suitable regiments for initial administration in booster shots are also variable but are typified by an initial administration followed by repeated doses at one or more hour intervals by a subsequent injection or other administration. Alternatively, continuous or intermittent intravenous infusions may be made sufficient to maintain concentrations of at least from about 10 nanomolar to 10 micromolar of the antibody in the blood.

In some instances, it may be desirable to modify the antibody of the present invention to impart a desirable biological, chemical or physical property thereto. More particularly, it may be useful to conjugate (i.e. covalently link) the antibody to a pharmaceutical agent, e.g. a fibrinolytic drug such as t-PA, streptokinase, or urokinase to provide fibrinolytic activity. Such linkage can be accomplished by several methods including use of a linking molecule such as a heterobifunctional protein cross-linking agent, e.g. SPDP, carbodimide, or the like, or by recombinant methods.

In addition to pharmaceuticals such as a fibrinolytic agent, an antibody of the invention can be conjugated to a toxin of e.g. plant or bacterial origin such as diphtheria toxin (i.e., DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. The toxin can also be an agent active at cell surfaces such as phospholipases (e.g., phospholipase C). As another example, the toxin can be a chemotherapeutic drug such as, e.g., vendesine, vincristine, vinblastin, methotrexate, adriamycin, bleomycin, or cisplatin, or, the toxin can be a radionuclide such as, e.g., iodine-131, yttrium-90, rhenium-188 or bismuth-212 (see generally, Moskaug et al., *J. Biol. Chem.*, 264:15709 (1989); I. Pastan et al., *Cell*, 47:641 (1986); Pastan et al., *Recombinant Toxins as Novel Therapeutic Agents, Ann. Rev. Biochem.*, 61:331 (1992); *Chimeric Toxins Olsnes and Phil, Pharmac. Ther.*, 25:355 (1982); published PCT Application No. WO 94/29350; published PCT Application No. WO 94/04689; and U.S. Pat. No. 5,620,939). Also, as discussed above, in addition to a toxin, an antibody of the invention can be conjugated to an effector molecule (e.g. IgG1 or IgG3) to provide complement-fixing ability and antibody-dependent cell-mediated cytoxicity upon administration to a mammal.

Such an antibody/cytotoxin or effector molecule conjugate can be administered in a therapeutically effective amount to a mammal, preferably a primate such as a human, where the mammal is known to have or is suspected of having tumor cells, immune system cells, or endothelia capable of expressing TF. Exemplary of such tumor cells, immune system cells and endothelia include malignancies of the breast and lung, monocytes and vascular endothelia.

Antibodies of the invention also can be conjugated to a variety of other pharmaceutical agents in addition to those described above such as, e.g., drugs, enzymes, hormones, chelating agents capable of binding a radionuclide, as well as other proteins and polypeptides useful for diagnosis or treatment of disease. For diagnostic purposes, the antibody of the present invention can be used either detectably-labelled or unlabelled. For example, a wide variety of labels may be suitably employed to detectably-label the antibody, such as radionuclides, fluors, enzymes, enzyme substrates, enzyme cofactors, enzyme inhibitors, ligands such as, e.g., haptens, and the like.

Diagnostic methods are also provided including in vivo diagnostic imaging [see, e.g., A. K. Abbas, *Cellular and Molecular Immunology*, pg. 328 (W. B. Saunders Co. 1991)]. For most in vivo imaging applications, an antibody of the invention can be detectably-labeled with, e.g., $^{125}$I, $^{32}$P, $^{99}$Tc, or other detectable tag, and subsequently administered to a mammal, particularly a human, for a pre-determined amount of time sufficient to allow the antibody to contact a desired target. The subject is then scanned by known procedures such as scintigraphic camera analysis to detect binding of the antibody. The analysis could aid in the diagnosis and treatment of a number of thromboses such as those specifically disclosed herein. The method is particularly useful when employed in conjunction with cardiac surgery, particularly angioplasty, or other surgical procedure where undesired formation of a blood clot can occur, to visualize the development or movement of a blood clot.

Antibodies of the invention also can be used to prepare substantially pure (e.g., at least about 90% pure, preferably at least about 96 or 97% pure) native TF, particularly native human TF from a biological sample. For example, native TF can be obtained as previously described (see e.g., L. V. M. Rao et al., *Thrombosis Res.*, 56:109 (1989)) and purified by admixing the solution with a solid support comprising the antibody to form a coupling reaction admixture. Exemplary solid supports include a wall of a plate such as a microtitre plate, as well as supports including or consisting of polystyrene, polyvinylchloride, a cross-linked dextran such as Sephadex™ (Pharmacia Fine Chemicals), agarose, polystyrene beads (Abbott Laboratories), polyvinyl chloride, polystyrene, polyacrylmide in cross-linked form, nitrocellulose or nylon and the like. The TF can then be isolated from the solid support in substantially pure form in accordance with standard immunological techniques. See generally Harlow and Lane supra and Ausubel et al. supra).

As also discussed above, antibodies of the invention can be employed to detect native human TF in a biological sample, particularly native TF associated with a blood clot. Exemplary biological samples include blood plasma, serum, saliva, urine, stool, vaginal secretions, bile, lymph, ocular humors, cerebrospinal fluid, cell culture media, and tissue, particularly vascular tissues such as cardiac tissue. Samples may be suitably obtained from a mammal suffering from or suspected of suffering from a thrombosis, preferably restenosis, associated with, e.g., an invasive medical procedure such as cardiopulmonary bypass surgery; a heart ailment such as myocardial infarction, cardiomyopathy, valvular heart disease, unstable angina, or artrial fibrillation associated with embolization; a coagulopathy including disseminated intravascular coagulation, deployment of an implementation such as a stent or catheter; shock (e.g., septic shock syndrome), vascular trauma, liver disease, heat stroke, malignancies (e.g., pancreatic, ovarian, or small lung cell carcinoma), lupus, eclampsia, perivascular occlusive disease, and renal disease.

For such assays, an antibody of the invention can be detectably-labelled with a suitable atom or molecule e.g., radioactive iodine, tritium, biotin, or reagent capable of generating a detectable product such as an anti-iodiotypic antibody attached to an enzyme such as β-galactosidase or horseradish peroxidase, or a fluorescent tag (e.g., fluorescein or rhodamine) in accordance with known methods. After contacting the biological sample with the detectably-labelled antibody, any unreacted antibody can be separated from the biological sample, the label (or product) is detected by conventional immunological methods including antibody capture assay, antibody sandwich assay, RIA, ELISA, immuno-precipitation, immunoabsorption and the like (see Harlow and Lane, supra; Ausubel et al. supra). Any label (or product) in excess of that detected in a suitable control sample is indicative of the presence of native TF, more particularly a blood clot, in the biological sample. For example, antibodies of the invention can be detectably-labelled to detect, and preferably quantitate, native TF in accordance with standard immunological techniques such as antibody capture assay, ELISA, antibody sandwich assay, RIA, immunoprecipitation, immunoabsorption and the like. In some cases, particularly when a tissue is used, the immunological technique may include tissue fixation with a reagent known to substantially maintain protein conformation (e.g., dilute formaldehyde). See generally, Ausubel et al., *Current Protocols in Molecular Biology*, John Wiley & Sons, New York, (1989); Harlow and Lane in *Antibodies: A Laboratory Manual*, CSH Publications, NY (1988).

Antibodies of the invention also can be used for detecting and purifying cells which express native TF, including fibroblasts, brain cells, immune cells, (e.g., monocytes), epithelia, as well as certain malignant cells. Preferred methods of detecting and purifying the cells include conventional immunological methods (e.g., flow cytometry methods such as FACS, and immunopanning). Substantially pure populations of cells expressing native TF are useful in clinical and research settings, e.g., to establish such cells as cultured cells for screening TF-binding antibodies.

The invention also provides test and diagnostic kits for detection of native TF, particularly native human TF, in a test sample, especially a body fluid such as blood, plasma, etc., or tissue as discussed above. A preferred kit includes a detectably-labelled antibody of the invention. The diagnostic kit can be used in any acceptable immunological format such as an ELISA format to detect the presence or quantity of native TF in the biological sample.

All documents mentioned herein are fully incorporated by reference in their entirety.

The following non-limiting examples are illustrative of the invention. In the following examples and elsewhere the antibodies H36 and H36.D2 are referred to. Those antibodies are the same antibody as H36.D2.B7, but H36 is derived from the mother clone, and H36.D2 is obtained from the primary clone, whereas H36.D2.B7 is obtained from the secondary clone. No differences have been observed between those three clones with respect to ability to inhibit TF or other physical properties.

EXAMPLE 1

Preparation and Cloning of Anti-rhTF Monoclonal Antibodies Monoclonal Antibodies Against rhTF were Prepared as Follows A. Immunization and Boosts Five female BALB/c mice were immunized with 10 μg each of lipidated, purified rhTF. The mice were initially sensitized intraperitoneally using Hunter's Titermax adjuvant. Three final boosts were administered in 0.85% NaCl. Boosts were 2, 5.5, and 6.5 months post initial sensitization. All boosts were given intraperitoneally, except the first which was subcutaneous. The final boost was given 3 days pre-fusion and 20 μg was administered.

B. Fusion of Mouse Spleen Lymphocytes with Mouse Myeloma Cells

Lymphocytes from the spleen of one rhTF immunized BALB/c mouse was fused to X63-Ag8.653 mouse myeloma cells using PEG 1500. Following exposure to the PEG, the cells were incubated for one hour in heat inactivated fetal bovine serum at 37° C. The fused cells were then resuspended in RPMI 1640 and incubated overnight at 37° C. with 10% $CO_2$. The cells were plated the next day using RPMI 1640 and supplemented with macrophage culture supernatant.

C. ELISA Development

Plates for the ELISA assay were coated with 100 microliters of recombinant tissue factor (0.25 μg/ml) in a carbonate based buffer. All steps were performed at room temperature. Plates were blocked with BSA, washed, and then the test samples and controls were added. Antigen/antibody binding was detected by incubating the plate with goat anti-mouse HRP conjugate (Jackson ImmunoResearch Laboratories) and then using an ABTS peroxidase substrate system (Kirkegaad and Perry Laboratories). Absorbance were read on an automatic plate reader at a wavelength of 405 nm.

D. Stabilization of rhTF Hybridoma Cell Lines

Two weeks after fusion, screening of hybridoma colonies by specific rhTF ELISA was started. Screening for new colonies continued for three weeks. The positive clones were tested every one to two weeks for continued antibody production until fifteen stable clones were frozen down.

E. Primary and Secondary Cloning

Limiting dilution cloning was performed on each of the positive stable hybridomas to obtain primary clones. The cells were thawed, grown in culture for a short period of time, and then diluted from 10 cells/well to 0.1 cells/well. Primary clones were tested by anti-rhTF ELISA and five to six positive clones were expanded and frozen.

Secondary clone of anti-rhTF antibody, H36.D2.B7, was obtained from primary clone, H36.D2, prepared and stored in liquid nitrogen as described above. Four different dilutions, 5 cells/well, 2 cells/well, 1 cell/well, 0.5 cells/well of the primary clone were prepared in 96-wells microtiter plates to start the secondary cloning. Cells were diluted in IMDM tissue culture media containing the following additives: 20% fetal bovine serum (FBS), 2 mM L-glutamine, 100 units/ml of penicillin, 100 μg/ml of streptomycin, 1% GMS-S, 0.075% $NaHCO_3$. To determine clones that secrete anti-rhTF antibody, supernatants from five individual wells of the 0.2 cells/well microtiter plate were withdrawn after two weeks of growth and tested for the presence of anti-rhTF antibody by ELISA assays as described above. All five clones showed positive results in the ELISA assay, with H36.D2.B7 being the best antibody producer. All five clones were adapted and expanded in RPMI media containing the following additive: 10% FBS, 2 mM L-glutamine, 100 units/ml of penicillin, 100 μg/ml of streptomycin, 1% GMS-S, 0.075% $NaHCO_3$, and 0.013 mg/ml of oxalaacetic acid. H36.D2.B7 was purified by Protein A affinity chromatography from the supernatant of cell culture and was tested for its ability to inhibit TF:VIIa in a FX activation assay. The results indicated that H36.D2.B7 had the same inhibition as H36.D2 antibody. All cells were stored in liquid nitrogen.

F. Isolation of total RNA from H36.D2.B7

269 μg of total RNA was isolated from $2.7 \times 10^5$ H36.D2.B7 hybridoma cells. The isolation of total RNA was performed as described in the RNeasy Midi Kits protocol from Qiagen. The RNA sample was stored in water at −20° C. until needed.

G. cDNA Synthesis and Cloning of Variable Regions of H36.D2.B7Gene

To obtain the first strand of cDNA, a reaction mixture containing 5 μg of total RNA isolated as above, back primers JS300 (all primers are identified below) for the heavy chain (HC) and OKA 57 for the light chain (LC), RNase inhibitor, dNTP's, DTT, and superscript II reverse transcriptase, was prepared and incubated at 42° C. for 1 hour. The reaction tube is then incubated at 65° C. for 15 minutes to stop the transcription. After cooling down, five units of RNase H was then added and the reaction was allowed to incubate at 37° C. for 20 minutes. The cDNA sample was stored at −70° C. until needed.

PCR (polymerise chain reaction) was conducted separately to clone the variable regions of both HC and LC of anti-rhTF, H36.D2.B7 from the cDNA made as above (nucleic acid and amino acid sequences of those HC and LC variable regions set forth in FIGS. 1A and 1B). Three rounds of PCR were conducted. Round 1: PCR was run for 35 cycles at 96° C., 53° C. and 72° C. using front primer JS002 and back primer JS300 for HC. For LC front primer JS009 and back primer OKA 57 were used and PCR was rune for 35 cycles at 96° C., 63° C. and 72° C. Round 2: PCR of both HC and LC was rune the same as in Round 1 with the exception that pMC-18 was used for HC front primer and pMC-15 for LC front primer. Round 3: PCR was run for 30 cycles at 96° C., 60-65° C. and 72° C. using H36HCF and H36HCR primers for HC. For LC, PCR was run for 30 cycles at 96° C., 58° C. and 72° C. using H36LCF and H36LCR primers.

The following primers were used for cloning H36.D2.B7 variable regions of HC and LC.

(SEQ ID NO: 17)
OKA 57:
5'-GCACCTCCAGATGTTAACTGCTC-3'

(SEQ ID NO: 18)
JS300:
5'-GAARTAVCCCTTGACCAGGC-3'

(SEQ ID NO: 19)
JS009:
5'-GGAGGCGGCGGTTCTGACATTGTGMTGWCMCARTC-3'

(SEQ ID NO: 20)
JS002:
5'-ATTTCAGGCCCAGCCGGCCATGGCCGARGTYCARCTKCARCARYC-Y (SEQ ID NO: 21)
pMC-15:
5'-CCCGGGCCACCATGKCCCCWRCTCAGYTYCTKG-3'

(SEQ ID NO: 22)
pMC-18:
5'-CCCGGGCCACCATGGRATGSAGCTGKGTMATSCTC-3'

(SEQ ID NO: 23)
H36HCF:
5'-ATATACTCGCGACAGCTACAGGTGTCCACTCCGAGATCCAGCTGCAG
CAGTC-3'

(SEQ ID NO: 24)
H36HCR:
5'-GACCTGAATTCTAAGGAGACTGTGAGAGTGG-3'

(SEQ ID NO: 25)
H36LCF:
5'-TTAATTGATATCCAGATGACCCAGTCTCC-3'

(SEQ ID NO: 26)
H36LCR:
TAATCGTTCGAAAAGTGTACTTACGTTTCAGCTCCAGCTTGGTCC where in the above SEQ ID NOS: 17 through 26: K is G or T; M is A or C; R is A or G; S is C or G; V is A, C or G; W is A or T; Y is C or T.

EXAMPLE 2

Binding Activity of Mabs of the Invention

Mabs of the invention as prepared in Example 1 above were employed. The rhTF molecule was expressed in *E. coli* and purified by immunoaffinity chromatography in accordance with standard methods (see Harlow and Lane, supra, Ausubel et al. supra). Mab association ($K_a$) and dissociation ($K_d$) constants were determined by ELISA and surface plasmon resonance (i.e., BIACore) assays (see e.g., Harlow and Lane, supra; Ausubel et al. supra; Altschuh et al., *Biochem.*, 31:6298 (1992); and the BIAcore method disclosed by Pharmacia Biosensor). For BIACore assays, rhTF was immobilized on a biosensor chip in accordance with the manufacturer's instructions. Constants for each Mab were determined at four antibody concentrations (0.125 nM, 0.25 nM, 0.5 nM, and 1 nM).

Protein concentrations were determined by standard assay (M. M. Bradford, *Anal. Biochem.*, 72:248 (1976)) using Bovine Serum Albumin as a standard and a commercially available dye reagent (Bio-Rad).

FIG. 2 shows association and disassociation constants for each anti-rhTF Mab. Mab H36 exhibited the highest association rate ($K_a=3.1\times10^{10}$ $M^{-1}$) and the lowest disassociation rate ($K_d=3.2\times10"$ M) of any of the anti-rhTF Mabs tested.

EXAMPLE 3

FXa-Specific Substrate Assay

In general, the experiments described herein were conducted using rhTF lipidated with phosphatidycholine (0.07 mg/ml) and phosphatidylserine (0.03 mg/ml) at a 70/30 w/w ratio in 50 mM Tris-HCl, pH 7.5, 0.1% bovine serum albumin (BSA) for 30 minutes at 37° C. A stock solution of preformed TF:VIIa complex was made by incubating 5 nM of the lipidated rhTF and 5 nM of FVIIa for 30 minutes at 37° C. The TF:VIIa complex was aliquoted and stored at −70° C. until needed. Purified human factors VII, VIIa, and FX were obtained from Enyzme Research Laboratories, Inc. The following buffer was used for all FXa and FVIIa assays: 25 mM Hepes-NaOH, 5 mM $CaCl_2$, 150 mM NaCl, 0.1% BSA, pH 7.5.

Mabs were screened for capacity to block TF:VIIa-mediated activation of FX to FXa. The FX activation was determined in two discontinuous steps. In the first step (FX activation), FX conversion to FXa was assayed in the presence of $Ca^{+2}$. In the second step (FXa activity assay), FX activation was quenched by EDTA and the formation of FXa was determined using a FXa-specific chromogenic substrate (S-2222). The S-2222 and S-2288 (see below) chromogens were obtained from Chromogenix (distributed by Pharmacia Hepar Inc.). FX activation was conducted in 1.5 ml microfuge tubes by incubating the reaction with 0.08 nM TF:VIIa, either pre-incubated with an anti-rhTF antibody or a buffer control. The reaction was subsequently incubated for 30 minutes at 37° C., then 30 nM FX was added followed by an additional incubation for 10 minutes at 37° C. FXa activity was determined in 96-well titre plates. Twenty microlitres of sample was withdrawn from step one and admixed with an equal volume of EDTA (500 mM) in each well, followed by addition of 0.144 ml of buffer and 0.016 ml of 5 mM S-2222 substrate. The reaction was allowed to incubate for an additional 15-30 minutes at 37° C. Reactions were then quenched with 0.05 ml of 50% acetic acid, after which, absorbance at 405 nm was recorded for each reaction. The inhibition of TF:VIIa activity was calculated from $OD_{405nm}$ values in the experimental (plus antibody) and control (no antibody) samples. In some experiments, an anti-hTF antibody, TF/VIIa, and FX were each added simultaneously to detect binding competition. FIG. 3 shows that the H36.D2 MAb (in bold) inhibited TF:/VIIa activity toward FX to a significantly greater extent (95%) than other anti-rHTF Mabs tested.

EXAMPLE 4

FVIIa-Specific Substrate Assay

Mabs were further screened by an FVIIa specific assay. In this assay, 5 nM lipidated rhTF was first incubated with buffer (control) or 50 nM antibody (experimental) in a 96-well titre plate for 30 minutes at 37° C., then admixed with 5 nM purified human FVIIa ($V_T$=0.192 ml), followed by 30 minutes incubation at 37° C. Eight microliters of a 20 mM stock solution of the FVIIa specific substrate S-2288 was then added to each well (final concentration, 0.8 mM). Subsequently, the reaction was incubated for one hour at 37° C. Absorbance at 405 nm was then measured after quenching with 0.06 ml of 50% acetic acid. Percent inhibition of TF/VIIa activity was calculated from $OD_{405\ nm}$ values from the experimental and control samples.

FIG. 4 shows the H36 antibody did not significantly block TF/VIIa activity toward the S-2288 substrate when the antibody was either pre-incubated with TF (prior to VIIa addition) or added to TF pre-incubated with VIIa (prior to adding the antibody). This indicates that H36 does not interfere with the interaction (binding) between TF and FVIIa, and that H36 also does not inhibit TF:VIIa activity toward a peptide substrate.

EXAMPLE 5

Prothrombin Time (PT) Assay

Calcified blood plasma will clot within a few seconds after addition of thromboplastin (TF); a phenomenon called the "prothrombin time" (PT). A prolonged PT is typically a useful indicator of anti-coagulation activity (see e.g., Gilman et al. supra).

The H36.D2 antibody was investigated for capacity to affect PT according to standard methods using commercially available human plasma (Ci-Trol Control, Level I obtained from Baxter Diagnostics Inc.). Clot reactions were initiated by addition of lipidated rhTF in the presence of $Ca^{++}$. Clot time was monitored by an automated coagulation timer (MLA Electra 800). PT assays were initiated by injecting 0.2 ml of lipidated rhTF (in a buffer of 50 mM Tris-HCl, pH 7.5, containing 0.1% BSA, 14.6 mM $CaCl_2$. 0.07 mg/ml of phosphatidylcholine, and 0.03 mg/ml of phosphatidylserine) into plastic twin-well cuvettes. The cuvettes each contained 0.1 ml of the plasma preincubated with either 0.01 ml of buffer (control sample) or antibody (experimental sample) for 1-2 minutes. The inhibition of TF-mediated coagulation by the H36.D2 antibody was calculated using a TF standard curve in which the log [TF] was plotted against log clot time.

FIG. 5 shows the H36.D2 antibody substantially inhibits TF-initiated coagulation in human plasma. The H36.D2 antibody increased PT times significantly, showing that the antibody is an effective inhibitor of TF-initiated coagulation (up to approximately 99% inhibition).

EXAMPLE 6

FX and the H36.D2 Antibody Compete For Binding to the TF: VIIa Complex

Competition experiments were conducted between TF/VIIa, FX and the H36.D2 antibody. FIG. 6A illustrates the results of an experiment in which a preformed TF/VIIa complex (0.08 nM) was pre-incubated at 37° C. for 30 minutes in buffer including 0.02 nM, 0.04 nM, 0.08 nM and 0.16 nM of the H36.D2 monoclonal antibody, respectively. FX (30 nM) was then added to the TF/VIIa and H36.D2 antibody mixture and the mixture allowed to incubate for an additional 10 minutes at 37° C. FX activation was quenched with EDTA as described previously. The FXa produced thereby was determined by the FXa-specific assay described in Example 3, above.

Figure 6B:
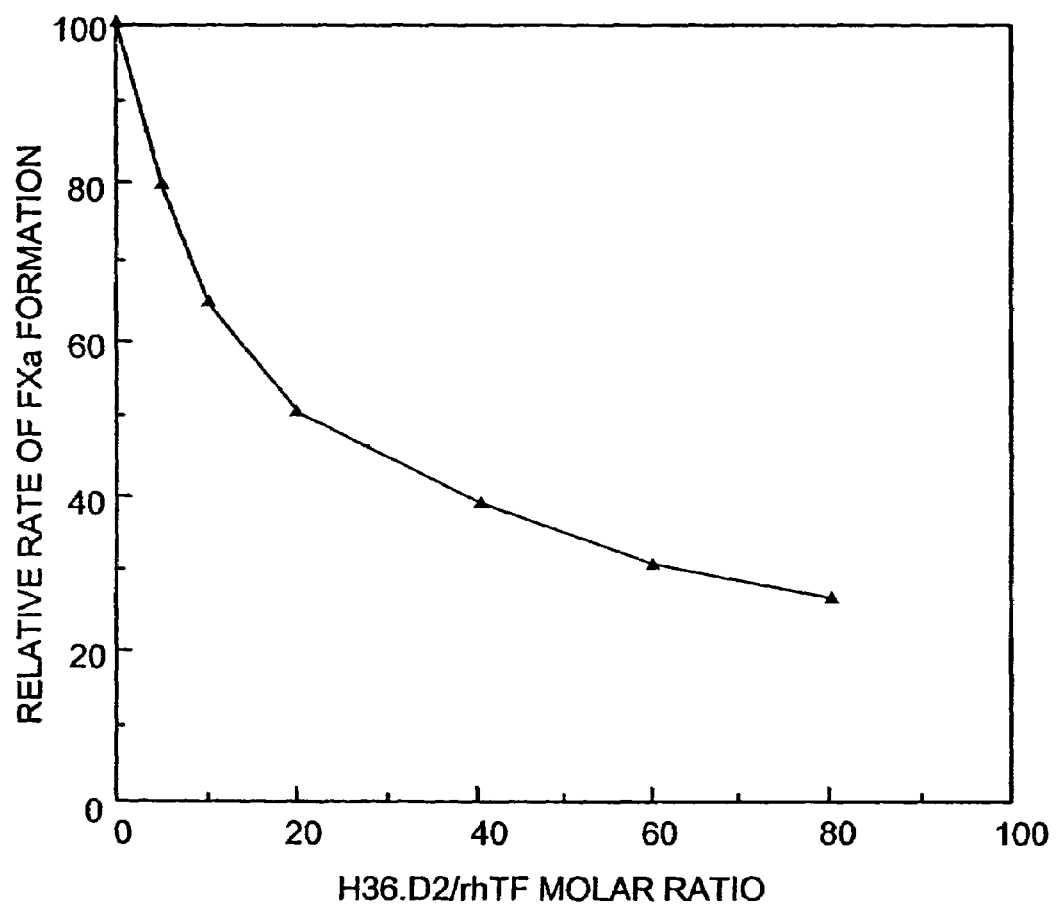

FIG. 6B shows the results of an experiment conducted along the lines just-described, except that the H36.D2 antibody, pre-formed TF:VIIa, and FX were added simultaneously to start the FX activation assay.

The data set forth in FIGS. 6A and 6B show that the H36.D2 antibody and FX compete for binding to the preformed TF/VIIa complex.

EXAMPLE 7

Inhibition of TF Activity in Cell Culture

J-82 is a human bladder carcinoma cell line (available from the ATCC) which abundantly expresses native human TF as a cell surface protein. To see if the H36.D2 antibody could prevent FX from binding to native TF displayed on the cell surface, a J-82 FX activation assay was conducted in microtitre plates in the presence of FVII (see D. S. Fair et al., *J. Biol. Chem.*, 262:11692 (1987)). To each well, $2\times10^5$ cells was added and incubated with either 50 ng FVII, buffer (control sample) or the anti-TF antibody (experimental sample) for 2 hours at 37° C. Afterwards, each well was gently washed with buffer and 0.3 ml of FX (0.05 mg/ml) was added to each well for 30 minutes at room temperature. In some cases, the antibody was added at the same time as FX to detect binding competition for the native TF. Thereafter, 0.05 ml aliquots were removed and added to new wells in a 96-well titre plate containing 0.025 ml of 100 mM EDTA. FXa activity was determined by the Fxa-specific assay as described in Example 3, above. Inhibition of TF activity on the surface of the J-82 cells was calculated from the $OD_{405\ nm}$ in the absence (control sample) and presence of antibody (experimental sample).

FIG. 7 shows that the H36.D2 antibody bound native TF expressed on J-82 cell membranes and inhibited TF-mediated activation of FX. These results indicate that the antibody competes with FX for binding to native TF displayed on the cell surface. Taken with the data of Example 8, below, the results also show that the H36.D2 antibody can bind a conformational epitope on native TF in a cell membrane.

EXAMPLE 8

Specific Binding of the H36.D2 Antibody to Native rhTF

Evaluation of H36.D2 binding to native and non-native rhTF was performed by a simplified dot blot assay. Specifically, rhTF was diluted to 30 μg/ml in each of the following three buffers: 10 mM Tris-HCl, pH 8.0; 10 mM Tris-HCl, pH 8.0 and 8 M urea; and 10 mM Tris-HCl, pH 8.0, 8 M urea and 5 mM dithiothreitol. Incubation in the Tris buffer maintains rhTF in native form, whereas treatment with 8M urea and 5 nM dithiothreitol produces non-native (denatured) rhTF. Each sample was incubated for 24 hours at room temperature. After the incubation, a Millipore Immobilon (7×7 cm section) membrane was pre-wetted with methanol, followed by 25 mM Tris, pH 10.4, including 20% methanol. After the membranes were air-dried, approximately 0.5 µl, 1 µl, and 2 µl of each sample (30 µg/ml) was applied to the membrane and air-dried. After blocking the membrane by PBS containing 5% (w/v) skim milk and 5% (v/v) NP-40, the membrane was probed with H36.D2 antibody, followed by incubation with a goat anti-mouse IgG peroxidase conjugate (obtained from Jackson ImmunoResearch Laboratories, Inc.). After incubation with ECL Western Blotting reagents in accordance with the manufacturer's instructions (Amersham), the membrane was wrapped with plastic film (Saran Wrap) and exposed to X-ray film for various times.

FIG. 8A shows that the H36.D2 Mab binds a conformational epitope on native TF in the presence of Tris buffer or Tris buffer with 8M urea (lanes 1 and 2). The autoradiogram was exposed for 40 seconds. However, when the native TF was denatured with 8M urea and 5 mM DTT, H36.D2 binding was significantly reduced or eliminated (lane 3). FIG. 8B shows an over-exposed autoradiogram showing residual binding of the H36.D2 antibody to non-native (i.e., denatured) rhTF. The over-exposure was for approximately 120 seconds. Treatment with 8M urea alone probably resulted in only partial denaturation of the native rhTF since the two disulfide bonds in TF are not reduced. It is also possible that the partially denatured TF may refold back to native confirmation during later blotting process when urea is removed. These results also clearly distinguish preferred antibodies of the invention which do not bind denatured TF from previously reported antibodies which do not selectively bind to a conformational epitope and bind to denatured TF (see U.S. Pat. No. 5,437,864 where in FIG. 18 Western Blot analysis shows binding to TF denatured by SDS).

EXAMPLE 9

Effects of H36 on Tumor Growth and Metastasis of Human Breast Cancer in Nude Mice Human breast cancer cell line MDA-MB-435 was provided. The cells were transfected with full length of human tissue factor gene to generate a cell line designated MDA-MB-435/TF. TF activity was measured using PT assay by adding 0.2×10$^6$ cells to human plasma with or without the chimeric anti-tissue factor antibody, cH36. To detect TF on the surface of MDA-MB-435/TF, cH36, was used as primary antibody and PE-conjugated anti-human Fc antibody was used for the immunofluorescent detection.

MDA-MB-435/TF expressed TF activity as determined by the PT assay, which was inhibited by H36 as shown by significantly prolonged PT time (FIG. 9B), suggesting the TF on the cell surface of MDA-MB-435/TF was active and responsible for the procoagulant activity. TF staining was observed on the cell surface of MDA-MB-435/TF cells.

Figure 9A:
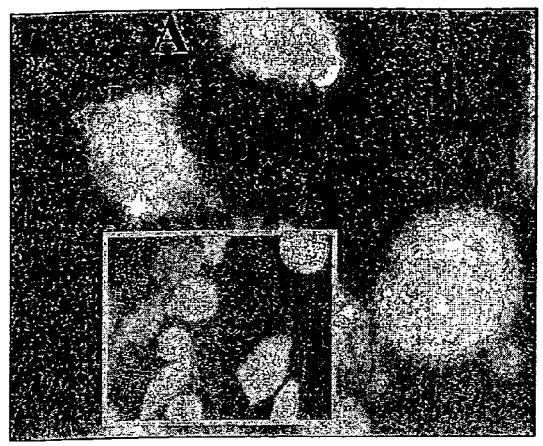
FIGS. 9A-C demonstrate presence of TF activity on the cell surface of a tumor cell.
Figure 9B:
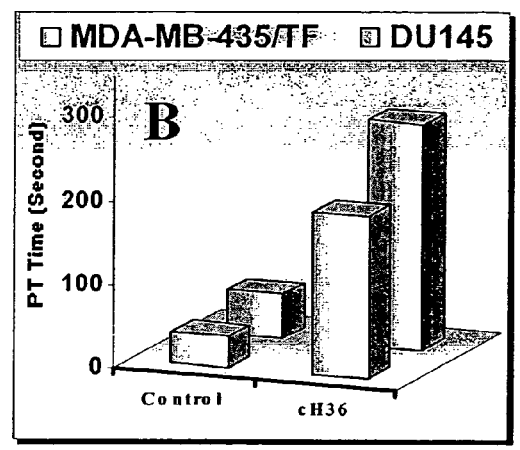
Figure 9C:
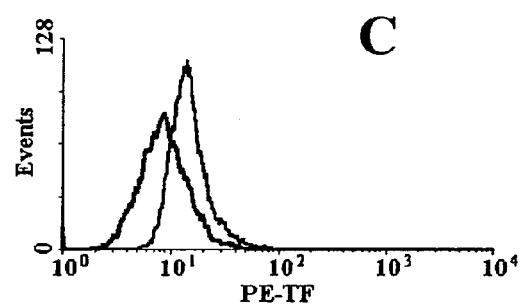

FIGS. 9A-C are explained in more detail as follows.

FIGS. 9A-C show inimunofluorescent detection of tumor cell surface TF antigen and determination of TF activity. Chimeric anti-human tissue factor antibody (called cH36), was used as primary antibody and PE-conjugated anti-human Fc antibody was used for the immunofluorescent detection of TF of MDA-MB-435/TF cells. TF staining was observed on the cell surface (FIG. 9A). Cells (0.2×10$^6$) are added to human plasma with or without chimeric anti-TF antibody, cH36; the cells only trigger clotting but show a prolonged clotting time in the presence of the antibody, indicating that the cell surface TF is being blocked (FIGS. 9B-C).

EXAMPLE 10

Effects of H36 on Tumor Growth and Metastasis of Human Colorectal Cancer in Nude Mice In this example, a human colorectal cancer cell line HT-29 was shown to express TF and the effects of H36 on growth and metastasis of this cell line were examined. The work was performed as described in Example 10 but with HT-29Lu3 used in place of MDA-MB 435/TF. The cell line HT-29Lu3 is a human colorectal adenocarcinoma that was derived by the authors from a lung metastasis nodule from a nude mouse injected with HT-29 (ATCC #HTB-38), and grown in McCoy's 5a medium supplemented with 10% fetal bovine serum, at 37° C. The study design is as follows:

| Group | # Mice | Time 0 (min) | Time 20 (min) |
|---|---|---|---|
| PBS | 8 | PBS 100 µL | HT-29Lu3, 200 µL |
| H36 | 8 | H36 100 µL(1 mg/kg) | HT-29Lu3, 200 µL |

The procoagulant activity of the HT-29Lu3 cells was shown by using them to initiate the PT assay. The PT time was prolonged by the anti-TF mAb H36 (FIGS. 10A-B), indicating that TF on the surface of HT29Lu3 cells is active and responsible for the coagulation in vitro. HT-29Lu3 Lysate exhibited higher TF activity, maybe due to the release of encrypted TF and/or phospholipids from the cells. Fixation of HT-29Lu3 in formalin (4% in PBS) also exhibited TF activity although decreased compared to the cells. Phosphotidylserine was detected on cell surface of HT-29Lu3 using Annexin-V binding assay.

Figure 10A:
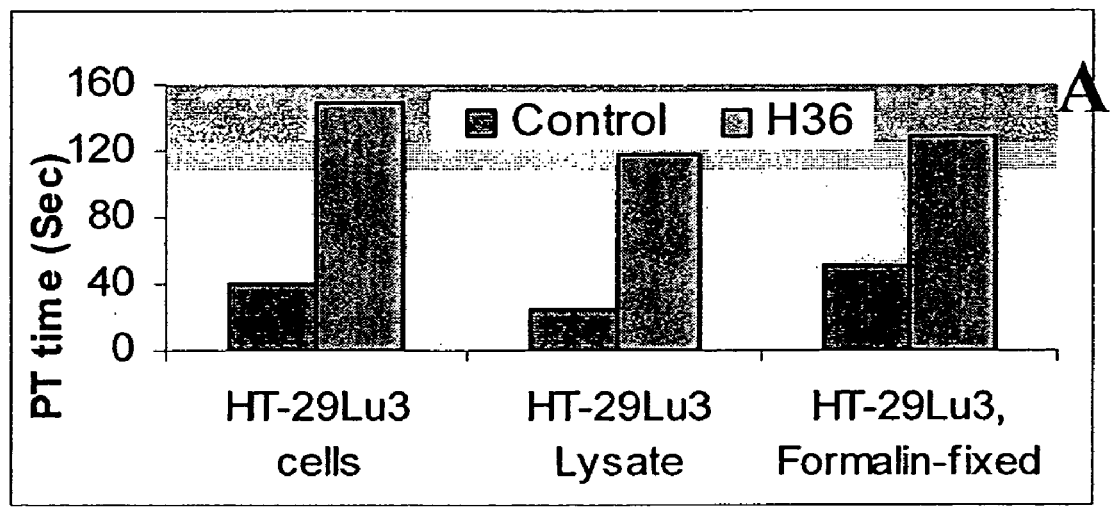
FIGS. 10A-B are graphs showing that HT-29Lu3 cells express TF activity and that use of H36 mAb inhibits the TF activity.
Figure 10B:
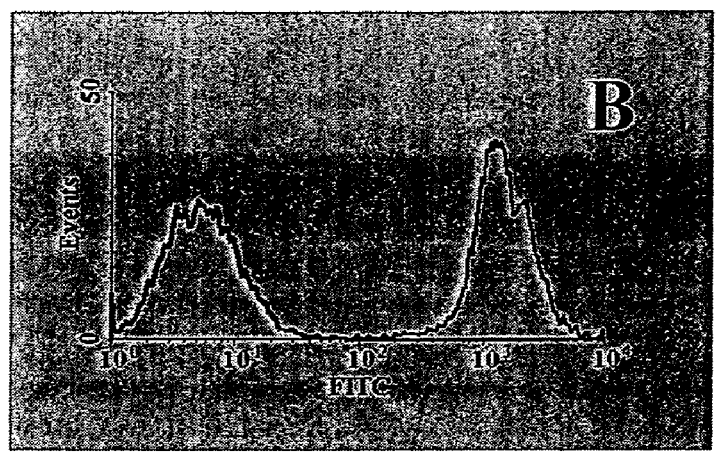

FIGS. 10A-B are described in more detail as follows.

FIGS. 10A-B show determination of TF activity (FIG. 10A) and TF antigen level (FIG. 10B) for HT-29Lu3 cells. The cells were used to trigger PT assay as stated in this Example and elsewhere herein. HT-29Lu3 cells initiated PT (FIG. 10A, dark bar) and PT time was prolonged by anti-TF mAB H36 (FIG. 10A, light bar), indicating that TF on the surface of HT29Lu3 cells is active and responsible for the coagulation in vitro. HT29Lu3 lysate exhibited higher TF activity which is consistent with release of encrypted TF and/or phospholipids form the cells. Fixation of HT-29Lu3 in formalin (4% in PBS) decreased TF activity. TF antigen on the cell surface could not be detected prior to permeabilization with MeOH and acetone (1:1). FIG. 10B shows the histogram of flow cytometric analysis of TF after permeabilization.

EXAMPLE 11

Detection and Imaging of Cancer

In the examples presented above, there are instances where it has been shown that the anti-TF antibodies can be used to detect or image cancer cells. For example, for the results shown in FIG. 9A, the chimeric anti-TF antibody cH36 was used to stain MDA-MB-435/TF cells, which was then detected by fluorescence using a PE-conjugated anti-human Fc antibody. FIGS. 9C, 10B demonstrated the usage of anti- TF antibody for the detection of cancer cells using flow cytometric method. FIG. 11A-E show that H36 can detect cancer cells (dark brown as indicated by the arrow) in lung tumors by immunohistochemical staining of TF. FIG. 11A-E is explained in more detail as follows.

Figure 11A:
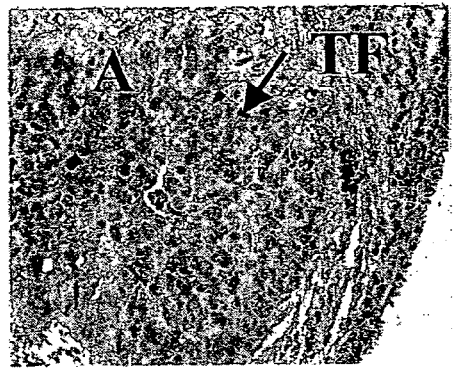
FIGS. 11A-E are photomicrographs showing immunohistochemical staining of sections from human lung carcinoma and normal human lung tissue for tissue factor and ErB2 expression.
Figure 11B:
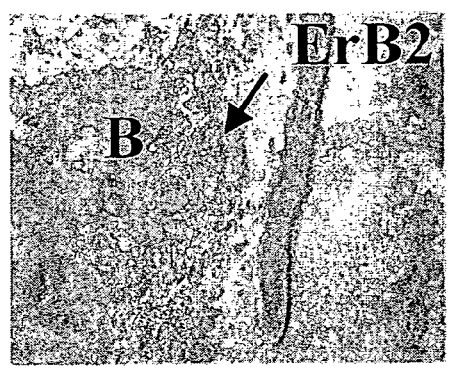
Figure 11C:
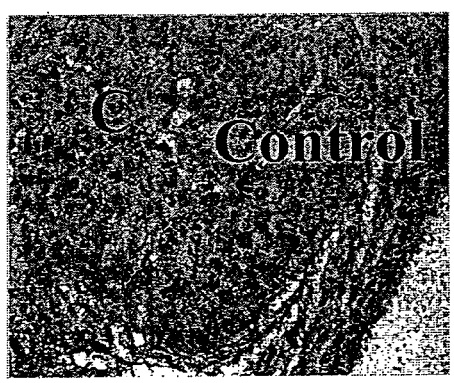
Figure 11D:
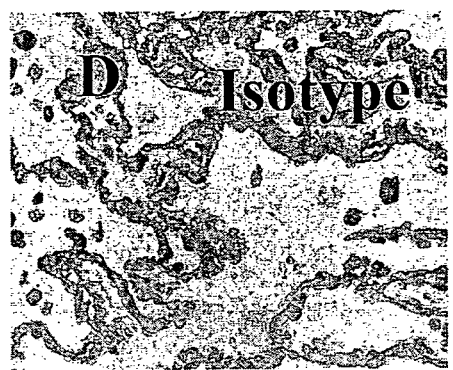
Figure 11E:
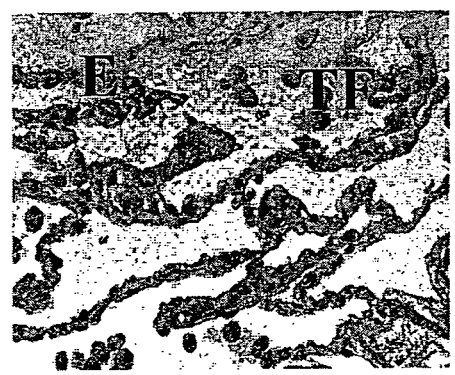

FIGS. 11A-E are micrographs of immunohistochemical staining of sections from human lung carcinoma and normal human lung tissue for tissue factor and ErB2 expression. H36 was used as the primary antibody. The detection was carried out using a Dako kit. Human lung tumor sample was detected as TF and ErB2 positive (FIGS. 11A and B, respectively) when compared to an isotype control (FIG. 11C). No TF was detected in normal human lung tissue (FIG. 11D, isotype control; FIG. 11E, H36 staining).

TF antigens on cell surface of human melanoma tumor A375-C15 cells and CHO-k1/TF cells were detected using-flow cytometric method as described earlier. See FIG. 12C, for instance. FIG. 12A shows that TF antigen is detected in CHO-k1/TF cells but no in parental CHO-k1 cells that do not express TF (FIG. 12B). TF was visualized using immunoflourescent staining. See FIG. 12C. Results are presented graphically in FIG. 12D.

FIGS. 12A-D are discussed in more detail as follows. The figures show detection and determination of TF antigen and its activity on CHO-k1/TF and CHO-k1 cells using a flow cytometric described earlier. See FIGS. 23A and B. Also shown are results of immunofluorescent staining (FIG. 12C) and prothrombin time (PT) assay (FIG. 12D) using anti-tissue factor antibody H36. TF antigen was detected on the surface of CHO-k1/TF cells (FIGS. 12A and C), but not on CHO-k1 cells (FIG. 12B). TF on CHO-k1/TF cells was active since it triggered blood coagulation in the PT assay and its activity was inhibited by anti-human TF antibody H36 (FIG. 12D), while CHO-k1 cells showed no TF activity in the PT assay.

The invention has been described in detail with reference to preferred embodiments thereof. However, it will be appreciated that those skilled in the art, upon consideration of the disclosure, may make modification and improvements within the spirit and scope of the invention.

What is claimed is:

1. A method for reducing tissue factor (TF) levels to treat tumors exhibiting tissue factor expression, comprising administering to a mammal having the tumor a therapeutically effective amount of an antibody that comprises the amino acid sequence of SEQ ID NO: 2 or SEQ ID NO:4, or fragment thereof that binds native human tissue factor to form a complex, whereby Factor X binding to the complex is inhibited and Factor VII or VIIa binding to tissue factor is not inhibited.

2. The method of claim 1, wherein the antibody or fragment has the binding specificity for native human tissue factor about equal to or greater than H36.D2.B7 deposited as ATCC HB12255.

3. The method of claim 1, wherein the antibody is H36.D2.B7 deposited as ATCC HB-12255.

4. The method of claim 1, wherein the antibody is a monoclonal antibody.

5. The method of claim 1, wherein the antibody is a chimeric antibody.

6. The method of claim 5, wherein the chimeric antibody further comprises a constant region of human origin.

7. The method of claim 1, wherein the antibody is a humanized antibody and comprises at least one hypervariable regions of non-human origin.

8. The method of claim 1, wherein the antibody is a single chain antibody.

9. The method of claim 1, wherein the fragment is a Fab, F(v), Fab', or F(ab')$_2$ fragment.

10. The method of claim 1, wherein the Factor X binding to the complex is inhibited by at least 80 percent in a standard in vitro binding assay.

11. The method of claim 1, wherein administration of the antibody increases the clotting time by at least 90 percent according to a prothrombin time (PT) assay.

12. The method of claim 5, wherein the chimeric antibody comprises a mouse variable region.

13. A method for reducing tissue factor (TF) levels to treat a tumor exhibiting tissue factor expression, comprising administering to a human having tumor a therapeutically effective amount of an anti-TF antibody that comprises six hypervariable regions which comprise sequences of SEQ ID NOs: 5-10 or a chimeric antibody of such anti-TF antibody.

14. The method of claim 13, wherein the antibody binds native human tissue factor to form a complex, whereby Factor X binding to the complex is inhibited and Factor VII or VIIa binding to tissue factor is not inhibited.

15. The method of claim 13, wherein the antibody is a chimeric antibody.

16. The method of claim 15, wherein the chimeric antibody comprises a mouse variable region.

17. The method of claim 13, wherein the antibody is a chimeric antibody and comprises the sequences of SEQ ID NO: 2 and SEQ ID NO: 4.

18. The method of claim 13, wherein the antibody comprises a constant region of human origin.

19. The method of claim 13, wherein the antibody is an immunologically active antibody fragment.

20. The method of claim 13, wherein the antibody is a Fab, F(v), Fab', or F(ab')$_2$.

21. The method of claim 13, wherein the antibody is a single chain antibody.

22. The method of claim 13, wherein the six hypervariable regions are encoded by the nucleic acid sequences of SEQ ID NOs: 11-16.

23. The method of claim 13, wherein the Factor X binding to the complex is inhibited by at least 80 percent in a standard in vitro binding assay.

24. The method of claim 13, wherein administration of the antibody increases the clotting time by at least 90 percent according to a prothrombin time (PT) assay.

* * * * *